(12) United States Patent
Sun et al.

(10) Patent No.: US 7,714,111 B2
(45) Date of Patent: May 11, 2010

(54) ARGININE DERIVATIVE WASH IN PROTEIN PURIFICATION USING AFFINITY CHROMATOGRAPHY

(75) Inventors: Shujun Sun, Brentwood, NH (US); Christopher Gallo, Windham, NH (US)

(73) Assignee: Wyeth LLC, Madison, NJ (US)

( * ) Notice: Subject to any disclaimer, the term of this patent is extended or adjusted under 35 U.S.C. 154(b) by 25 days.

(21) Appl. No.: 11/899,955

(22) Filed: Sep. 7, 2007

(65) Prior Publication Data

US 2008/0064860 A1    Mar. 13, 2008

Related U.S. Application Data

(60) Provisional application No. 60/843,084, filed on Sep. 8, 2006.

(51) Int. Cl.
*A61K 39/395* (2006.01)
*C07K 16/00* (2006.01)
*C07K 1/22* (2006.01)

(52) U.S. Cl. .............. 530/390.1; 424/176.1; 424/177.1; 530/390.5; 530/413

(58) Field of Classification Search ........................ None
See application file for complete search history.

(56) References Cited

U.S. PATENT DOCUMENTS

| | | | |
|---|---|---|---|
| 4,010,148 A | 3/1977 | Goldstein | |
| 4,230,697 A | 10/1980 | Nishida et al. | |
| 4,250,084 A | 2/1981 | Trainin | |
| 4,275,056 A | 6/1981 | Takaku et al. | |
| 4,304,864 A | 12/1981 | Numa et al. | |
| 4,350,625 A | 9/1982 | Abe | |
| 4,390,468 A | 6/1983 | Sasaki et al. | |
| 4,444,760 A | 4/1984 | Thomas, Jr. | |
| 4,452,735 A | 6/1984 | Wissler et al. | |
| 4,452,782 A | 6/1984 | Takemoto et al. | |
| 4,456,676 A | 6/1984 | Ciskowski | |
| 4,465,669 A | 8/1984 | Wissler et al. | |
| 4,512,970 A | 4/1985 | Wissler et al. | |
| 4,532,207 A | 7/1985 | Brewer et al. | |
| 4,552,761 A | 11/1985 | Wissler et al. | |
| 4,568,545 A | 2/1986 | Mihara et al. | |
| 4,604,234 A | 8/1986 | Fujii et al. | |
| 4,624,932 A | 11/1986 | Bogoch | |
| 4,639,513 A | 1/1987 | Hou et al. | |
| 4,656,158 A | 4/1987 | Matsuo et al. | |
| 4,657,891 A | 4/1987 | Matsuo et al. | |
| 4,670,539 A | 6/1987 | Sirbasku et al. | |
| 4,880,914 A | 11/1989 | Saxena et al. | |
| 4,882,421 A | 11/1989 | Shogen et al. | |
| 4,957,864 A | 9/1990 | Takahashi et al. | |
| 4,966,888 A | 10/1990 | Saxena et al. | |
| 5,030,559 A | 7/1991 | Nicolson et al. | |
| 5,093,241 A | 3/1992 | Bennett et al. | |
| 5,132,214 A | 7/1992 | Feder et al. | |
| 5,151,498 A | 9/1992 | Beuscher et al. | |
| 5,162,507 A | 11/1992 | Wolfe et al. | |
| 5,213,970 A | 5/1993 | Lopez-Berestein et al. | |
| 5,252,217 A | 10/1993 | Burnouf-Radosevich et al. | |
| 5,302,699 A | 4/1994 | Kawamura et al. | |
| 5,330,972 A | 7/1994 | Cope | |
| 5,332,503 A | 7/1994 | Lee et al. | |
| 5,372,942 A | 12/1994 | McGarrity et al. | |
| 5,424,287 A | 6/1995 | Bauer et al. | |
| 5,457,181 A | 10/1995 | Michalski et al. | |
| 5,478,924 A | 12/1995 | Cramer et al. | |
| 5,500,413 A | 3/1996 | Larsson et al. | |
| 5,559,211 A | 9/1996 | Kumagai et al. | |
| 5,621,073 A | 4/1997 | Dickhardt et al. | |
| 5,659,017 A | 8/1997 | Bhattacharya et al. | |
| 5,710,126 A * | 1/1998 | Griffith et al. | 514/12 |
| 5,756,687 A | 5/1998 | Denman et al. | |
| 5,760,183 A | 6/1998 | Dazey et al. | |
| 5,866,006 A | 2/1999 | Lihme et al. | |
| 6,043,067 A | 3/2000 | Lihme et al. | |
| 6,090,921 A | 7/2000 | Winge et al. | |
| 6,127,526 A | 10/2000 | Blank | |
| 6,128,336 A | 10/2000 | Rossi | |
| 6,281,336 B1 | 8/2001 | Laursen et al. | |
| 6,342,224 B1 * | 1/2002 | Bruck et al. | 424/192.1 |

(Continued)

FOREIGN PATENT DOCUMENTS

EP    0538350    4/1993

(Continued)

OTHER PUBLICATIONS

Arakawa, et al., "Elution of Antibodies from a Protein-A Column by Aqueous Arginine Solutions", Protein Expression and Purification, 36:244-248 (2004).

(Continued)

*Primary Examiner*—David A Saunders
(74) *Attorney, Agent, or Firm*—Gloria K. Szakiel; Christopher H. Chung

(57) ABSTRACT

The invention relates to methods for isolating a product and/or reducing turbidity and/or impurities from a load fluid comprising the product and one or more impurities by passing the load fluid through a medium, followed by at least one wash solution comprising an arginine derivative, and collecting the product using an elution solution. The invention further relates to a product prepared using a method as described herein.

47 Claims, 6 Drawing Sheets

U.S. PATENT DOCUMENTS

| | | |
|---|---|---|
| 6,451,260 B1 | 9/2002 | Dusterhoft et al. |
| 6,551,801 B1 | 4/2003 | Andou et al. |
| 6,593,097 B1 | 7/2003 | Xu |
| 6,670,455 B1 | 12/2003 | Roemisch et al. |
| 6,673,629 B2 | 1/2004 | Yoshimura et al. |
| 6,677,299 B2 * | 1/2004 | Stern et al. ............... 514/1 |
| 6,677,440 B1 | 1/2004 | Roemisch et al. |
| 6,770,457 B1 | 8/2004 | You et al. |
| 6,774,102 B1 | 8/2004 | Bell et al. |
| 6,870,034 B2 | 3/2005 | Breece et al. |
| 6,902,920 B2 | 6/2005 | Sobek et al. |
| 6,905,849 B1 | 6/2005 | Barton et al. |
| 6,939,545 B2 | 9/2005 | Jacobs et al. |
| 7,223,848 B2 | 5/2007 | Coffman et al. |
| 2002/0157125 A1 | 10/2002 | Lee et al. |
| 2003/0036629 A1 | 2/2003 | Foster et al. |
| 2003/0044848 A1 | 3/2003 | Rush et al. |
| 2003/0050450 A1 | 3/2003 | Coffman et al. |
| 2003/0118592 A1 | 6/2003 | Ledbetter et al. |
| 2003/0133939 A1 | 7/2003 | Ledbetter et al. |
| 2003/0157106 A1 | 8/2003 | Jacobs et al. |
| 2004/0058445 A1 | 3/2004 | Ledbetter et al. |
| 2004/0142382 A1 | 7/2004 | Veldman et al. |
| 2004/0161776 A1 | 8/2004 | Maddon et al. |
| 2004/0203115 A1 | 10/2004 | Giardina et al. |
| 2005/0003450 A1 | 1/2005 | Rush et al. |
| 2005/0042220 A1 | 2/2005 | Li et al. |
| 2005/0107594 A1 | 5/2005 | Sun et al. |
| 2005/0136049 A1 | 6/2005 | Ledbetter et al. |
| 2005/0153400 A1 | 7/2005 | Jacobs et al. |
| 2005/0158712 A1 | 7/2005 | Leboulch et al. |
| 2005/0158760 A1 | 7/2005 | Jacobs et al. |
| 2005/0175614 A1 | 8/2005 | Ledbetter et al. |
| 2005/0176109 A1 | 8/2005 | Yumioka et al. |
| 2005/0180970 A1 | 8/2005 | Ledbetter et al. |
| 2005/0186216 A1 | 8/2005 | Ledbetter et al. |
| 2005/0202012 A1 | 9/2005 | Ledbetter et al. |
| 2005/0202023 A1 | 9/2005 | Ledbetter et al. |
| 2005/0202028 A1 | 9/2005 | Ledbetter et al. |
| 2005/0202534 A1 | 9/2005 | Ledbetter et al. |
| 2005/0238646 A1 | 10/2005 | Ledbetter et al. |
| 2006/0063228 A1 | 3/2006 | Kasaian et al. |
| 2006/0073148 A1 | 4/2006 | Tchistiakova et al. |

FOREIGN PATENT DOCUMENTS

| | | |
|---|---|---|
| EP | 0607998 | 7/1994 |
| EP | 1568710 | 8/2005 |
| JP | 05018950 | 1/1993 |
| RU | 2143492 | 12/1999 |
| RU | 2144082 | 1/2000 |
| WO | WO-92/16623 | 10/1992 |
| WO | WO-93/03375 | 2/1993 |
| WO | WO-94/04678 | 3/1994 |
| WO | WO-97/26321 | 7/1997 |
| WO | WO-99/31120 | 6/1999 |
| WO | WO-01/18055 | 3/2001 |
| WO | WO-02/098531 | 12/2002 |
| WO | WO-2005/044856 | 5/2005 |

OTHER PUBLICATIONS

Barron, et al., "Improving Purity on Protein A Affinity Chromatography Media through use of an Arginine Intermediate Wash Step", IP.com—Prior Art Database, IPCOM00127319D, Aug. 22, 2005.

Bencina, et al., "Enzyme Immobilization on Epoxy- and 1,1'-Carbonyldiimidazole-Activated Methacrylate-Based Monoliths", Journal of Separation Science, 27(10-11):811-818 (2004).

Bird, et al., "Single-Chain Antigen-Binding Proteins", Science, 242:423-426 (1988).

Bost, et al., "In Vivo Treatment with Anti-Interleukin-13 Antibodies Significantly Reduces the Humoral Immune Response Against an Oral Immunogen in Mice", Immunology, 87:633-641 (1996).

Chao, et al., "Isolation of Tissue Kallikrein in Rat Spleen by Monoclonal Antibody-Affinity Chromatography", Biochimica et Biophysica Acta, 801(2):244-249 (1984).

Chartier Harlan, et al., "Early-Onset Alzheimer's Disease Caused by Mutations at Codon 717 of the β-Amyloid Precursor Protein Gene", Nature, 353:844-846 (1991).

Derynck, et al., "Human Transforming Growth Factor-β Complementary DNA Sequence and Expression in Normal and Transformed Cells", Nature, 316:701-705 (1995).

DiLorenzo, et al., "Serum Levels of Soluble CD23 in Patients with Asthma or Rhinitis Monosensitive to Parietaria. Its Relation to Total Serum IgE Levels and Eosinophil Cationic Protein during and out of the Pollen Season", Allergy Asthma Proc., 20(2):119-125 (1999).

Dumoutier, et al., "Human Interleukin-10-Related T Cell-Derived Inducible Factor: Molecular Cloning and Functional Characterization as an Hepatocyte-Stimulating Factor", Proc. Natl. Acad. Sci. USA, 97(18):10144-10149 (2000).

Ejima, et al., "Effective Elution of Antibodies by Arginine and Arginine Derivatives in Affinity Column Chromatography", Analytical Biochemistry, 345:250-257 (2005).

Gagnon, "Chapter 10: Other Bioaffinity Chromatography Methods", in Purification Tools for Monoclonal Antibodies, pp. 199-200.

Gamer, et al., "A Novel BMP Expressed in Developing Mouse Limb, Spinal Cord, and Tail Bud Is a Potent Mesoderm Inducer in Xenopus Embryos", Dev. Biol., 208:222-232 (1999).

Gentry, et al., "The Pro Domain of Pre-Pro-Transforming Growth Factor β1 When Independently Expressed Is a Functional Binding Protein for the Mature Growth Factor", Biochemistry, 29:6851-6857 (1990).

Goate, et al., "Segregation of a Missense Mutation in the Amyloid Precursor Protein Gene with Familial Alzheimer's Disease", Nature, 349:704-706 (1991).

Golovanov, et al., "A Simple Method for Improving Protein Solubility and Long-Term Stability", Journal of American Chemical Society, 126:8933-8939 (2004).

Herrera-Valdez, "Purification, Analysis and Synthesis of Proteins".

Ho, et al., "The Likelihood of Aggregation During Protein Renaturation can be Assessed Using the Second Virial Coefficient", Protein Science, 12:708-716 (2003).

Hoodless, et al., "Mechanism and Function of Signaling by th eTGFβ Superfamily", Curr. Topics Microbiol. Immunol., 228:235-272 (1998).

Huston, et al., "Protein Engineering of Antibody Binding Sites: Recovery of Specific Activity in an Anti-Digoxin Single-Chain Fv Analogue Produced in *Escherichia coli*", Proc. Natl. Acad. Sci. USA, 85:5879-5883 (1988).

International Search Report and Written Opinion from International Application No. PCT/US07/77865 mailed Aug. 5, 2008.

Kingsley, et al., "The TGF-beta Superfamily: New Members, New Receptors, and New Genetic Tests of Function in Different Organisms", Genes Dev., 8:133-146 (1994).

Kita, et al., "Contribution of the Surface Free Energy Perturbation to Protein—Solvent Interactions", Biochemistry, 33:15178-15189 (1994).

Kostelny, et al., "Formation of a Bispecific Antibody by the Use of Leucine Zippers", J. Immunol., 148:1547-1553 (1992).

Mann, "Current Trends and Future Solutions for the Clarification and Capture of Monoclonal Antibodies", Millipore Technology Workshop IBC Antibody Development & Production, Mar. 2, 2006.

Massague, "The Transforming Growth Factor-β Family", Ann. Rev. Cell Biol., 6:597-641 (1990).

McKenzie, et al., "Interleukin 13, a T-cell-derived Cytokine that Regulages Human Monocyte and B-Cell Function", Proc. Natl. Acad. Sci. USA, 90:3735-3739 (1993).

McPherron, et al., "Double Muscling in Cattle Due to Mutations in the Myostatin Gene", Proc. Nat. Acad. Sci. USA, 94:12457-12461 (1997).

Millipore Technical Brief, "Increasing Purity on ProSep-vA Affinity Chromatography Media using an Intermediate Wash Step", Lit. No. TB1026EN00 (2006).

Miyazono, et al., "Latent High Molecular Weight Complex of Transforming Growth Factor β1", J. Biol. Chem., 263(13):6407-6415 (1988).

Mullan, et al., "A Pathogenic Mutation for Probable Alzheimer's Disease in the APP Gene at the N-Terminus of β-Amyloid", Nature Genetics, 1:345-347 (1992).

Murrell, et al., "A Mutation in the Amyloid Precursor Protein Associated with Hereditary Alzheimer's Disease", Science, 254:97-99 (1991).

Narayanan, "Preparative Affinity Chromatography of Proteins", Journal of Chromotography A, 658:237-258 (1994).

Pittman, et al., "IL-22 is a Tightly-Regulated IL 10-Like Molecule that Induces an Acute-Phase Response and Renal Tubular Basophilia", Genes and Immunity: Abstracts—3rd International IL-10 Workshop, p. 172 (2001).

Schmidt, et al., "Stringent Purification of Recombinant Proteins Using WW/Polyproline Affinity Chromatography", International Journal of Bio-Chromatography, 6(1):79-85 (2001).

Songsivilai, et al., "Bispecific Antibody: A Tool for Diagnosis and Treatment of Disease", Clin. Exp. Immunol., 79:315-321 (1990).

Thies, et al., "GDF-8 Propeptide Binds to GDF-8 and Antagonizes Biological Activity by Inhibiting GDF-8 Receptor Binding", Growth Factors, 18:251-259 (2001).

Tomkinson, et al., "A Murine IL-4 Receptor Antagonist that Inhibits IL-4- and IL-13-Induced Responses Prevents Antigen-Induced Airway Eosinophilia and Airway Hyperresponsiveness", J. Immunol., 166:5792-5800 (2001).

Tsumoto, et al., "Highly Efficient Recovery of Functional Single-Chain Fv Fragments from Inclusion Bodies Overexpressed in *Escherichia coli* by Controlled Introduction of Oxidizing Reagent—Application to a Human Single-Chain Fv Fragment", Journal of Immunological Methods, 219:119-129 (1998).

Tsumoto, et al., "Role of Arginine in Protein Refolding, Solubilization, and Purification", Biotechnol. Prog., 20:1301-1308 (2004).

Wakefield, et al., "Latent Transforming Growth Factor-β from Human Platelets", J. Biol. Chem., 263(16):7646-7654 (1988).

Wills-Karp, et al., "Interleukin-13: Central Mediator of Allergic Asthma", Science, 282:2258-2261 (1998).

* cited by examiner

ARGININE DERIVATIVE WASH IN PROTEIN PURIFICATION USING AFFINITY CHROMATOGRAPHY

CROSS REFERENCE TO RELATED APPLICATION

This application claims the benefit of priority under 35 U.S.C. §119(e) to U.S. Patent Application Ser. No. 60/843,084 filed Sep. 8, 2006, which is hereby incorporated by reference in its entirety.

TECHNICAL FIELD

This application relates to protein purification. In particular, this application relates to methods for purifying a protein bound to a medium by passing at least one wash solution containing arginine or an arginine derivative through the medium, and collecting the purified protein.

BACKGROUND

With the advent of recombinant protein technology, a protein of interest can be produced using cultured eukaryotic or prokaryotic host cell lines engineered to express the protein. The use of the desired recombinant protein for pharmaceutical applications is generally contingent on being able to reliably recover adequate levels of the protein from impurities such as host cell proteins, protein variants, and compounds from the culture medium.

Conventional protein purification methods are designed to separate the protein of interest from impurities based on differences in size, charge, solubility, and degree of hydrophobicity. Such methods include chromatographic methods such as affinity chromatography, ion exchange chromatography, size exclusion chromatography, hydrophobic interaction chromatography, immobilized metal affinity chromatography, and hydroxyapatite chromatography. These methods often employ a separation medium that can be designed to selectively adhere either the protein of interest or the impurities. In the bind-elute mode, the desired protein selectively binds to the separation medium and is differentially eluted from the medium by different solvents. In the flow-through mode, the impurities specifically bind to the separation medium while the protein of interest does not, thus allowing the recovery of the desired protein in the "flow-through."

Current methods for the purification of proteins, such as antibodies, include two or more chromatographic steps. For example, the first step in the protein purification protocol can involve an affinity chromatography step that utilizes a specific interaction between the protein of interest and an immobilized capture reagent. Protein A adsorbents are particularly useful for affinity capture of proteins such as antibodies that contain an Fc region. However, there are numerous drawbacks to using Protein A chromatography for protein purification. In some instances, leakage of the Protein A capture agent results in contamination of the eluted protein product, while in other instances, affinity capture does not separate protein variants, such as aggregated forms of the protein, from the protein of interest. Additionally, varying levels of turbidity and/or precipitates can be formed in the Protein A elution pool following pH neutralization. This turbidity and/or precipitation can lead to significant product losses in the neutralized Protein A elution pool. Accordingly, there is a need for purification methods that reduce product losses and enhance the product purity in the elution pool.

SUMMARY OF THE INVENTION

The invention relates to methods, in part, for isolating a product from a load fluid that contains a product, such as an antibody, and one or more impurities by passing the load fluid through a medium that binds the product, followed by passing at least one wash solution containing arginine or an arginine derivative through the medium, and collecting the product using an elution solution.

In one aspect, a method for isolating a product is provided. The method comprises providing a load fluid comprising a product and one or more impurities and contacting the load fluid with a medium that can bind the product under conditions suitable for binding the product, thereby obtaining a bound medium. The method further comprises contacting the bound medium with one or more wash solutions comprising arginine or an arginine derivative, thereby obtaining a washed medium. The method further comprises contacting the washed medium with an elution solution under conditions suitable for eluting the product. The eluate comprising the product may then be collected. The product may also be further purified and/or formulated for therapeutic use.

In some embodiments of this aspect, the product is a protein, e.g., a therapeutic protein. In certain embodiments, the product is an antibody. In specific embodiments, the antibody is directed against or raised to one of the following: Growth and Differentiation Factor-8 (GDF-8), interleukin-13 (IL-13), interleukin-22 (IL-22), A-Beta, Receptor for Advanced Glycation End products (RAGE), and 5T4. In some embodiments, the product is an antigen-binding fragment. In some embodiments the product is a fusion protein. In specific embodiments, the product is an Ig-fusion protein. In certain embodiments, the product is an Fc-protein, an immunoconjugate, a cytokine, an interleukin, a hormone, or a therapeutic enzyme.

In some embodiments of this aspect, the medium is a matrix, a resin, or a chromatography column. In specific embodiments, the medium is a Protein A chromatography column, e.g., a recombinant Protein A column, or a Protein G chromatography column, e.g., a recombinant Protein G column.

In some embodiments of this aspect, the concentration of arginine or arginine derivative in the wash solution is about 0.1 M to about 2.0 M. In certain embodiments, the concentration of arginine or arginine derivative in the wash solution is about 0.1 M to about 0.9 M. In one embodiment, the concentration of arginine or arginine derivative in the wash solution is about 1 M. In certain other embodiments, the concentration of arginine or arginine derivative in the wash solution is about 1.1 M to about 2.0 M. In yet other embodiments, the concentration of arginine or arginine derivative in the wash solution is about 0.5 M to about 1.0 M. In yet other embodiments, the concentration of arginine or arginine derivative in the wash solution is greater than about 0.5 M and less than about 2.0 M. In another embodiment, the concentration of arginine or arginine derivative in the wash solution is greater than about 0.5 M and less than about 1.0 M. In specific embodiments, the arginine derivative is acetyl arginine, agmatine, arginic acid, N-alpha-butyroyl-L-arginine, or N-alpha-pyvaloyl arginine.

In some embodiments of this aspect, the pH of the wash solution is about 4.5 to about 8.0. In certain embodiments, the pH of the wash solution is greater than about 4.5 and less than about 8.0. In some embodiments, the pH of the wash solution is about 7.5.

In some embodiments of this aspect, the elution solution comprises one of: sodium chloride, arginine or an arginine derivative, glycine, HEPES, and acetic acid. In certain embodiments, the elution buffer has a pH of about 2.0 to about 4.0. In a specific embodiment, the elution buffer has a pH of about 3.0.

In certain embodiments of this aspect, one or more of the impurities is a host cell protein, a nucleic acid, a product variant, an endotoxin, Protein A, Protein G, a virus or a fragment thereof, a component from the cell culture medium, or product variant, e.g., underdisulfide-bonded product, low molecular weight product, high molecular weight product, truncated product and/or misfolded product. In some embodiments, wherein at least one impurity is bound to the product, the bound medium is contacted with one or more wash solutions through the bound medium thereby removing at least one impurity that is bound to the product.

In certain embodiments of this aspect, the eluate comprises an isolated product and the purity of the isolated product is increased compared to a corresponding method in which less than about 0.1 M of arginine or arginine derivative is used in a wash solution. In some embodiments, the eluate comprises an isolated product, and the ratio of the product to at least one impurity is increased compared to a corresponding method in which no detectable amount of arginine or arginine derivative is used in a wash solution. In certain embodiments, the eluate comprises a product, wherein the ratio of the product to host cell protein is increased compared to a corresponding method in which less than about 0.1 M of arginine or arginine derivative is used in a wash solution. In still further embodiments, the eluate comprises a product, wherein the ratio of the product to host cell protein is increased compared to a corresponding method in which no detectable amount of arginine or arginine derivative is used in a wash solution.

In another embodiment of this aspect, the turbidity of the eluate is reduced compared to a corresponding method in which less than about 0.1 M of arginine or arginine derivative is used in a wash solution. In some embodiments, the turbidity of the eluate is reduced compared to a corresponding method in which no detectable amount of arginine or arginine derivative is used in a wash solution.

In another aspect, a method of isolating an antibody is provided. The method comprises providing a load fluid comprising the antibody and one or more impurities, and contacting the load fluid with a Protein A medium or a Protein G medium, wherein the medium can bind the antibody under conditions suitable for binding the antibody, thereby resulting in a bound medium. The method further comprises contacting the bound medium with one or more wash solutions, wherein at least one wash solution comprises arginine or an arginine derivative in a concentration greater than 0.5 M and less than about 1.0 M, thereby providing a washed medium. The method further comprises contacting the washed medium with an elution solution under conditions suitable for eluting the antibody; and collecting an eluate comprising the antibody. As a result of practicing this method, the ratio of the antibody to host cell protein in the eluate is increased and the eluate has reduced turbidity compared to an eluate recovered in a corresponding method in which no detectable amount of arginine is used in a wash solution.

In some embodiments of this aspect, the pH of the wash solution is greater than about 5.0 and less than about 8.0.

In another aspect, a method for reducing turbidity in an eluate comprising a product is provided. The method comprises providing a load fluid comprising the product and one or more impurities, and contacting the load fluid with a medium, wherein the medium can bind the product under conditions suitable for binding the product, thereby providing a bound medium. The method further comprises contacting the bound medium with one or more wash solutions, wherein at least one wash solution comprises arginine or an arginine derivative, thereby providing a washed medium. The method further comprises contacting the washed medium with an elution solution under conditions suitable for eluting the product, thereby generating an eluate comprising the product, and neutralizing the pH of the eluate. The method provides an eluate that has reduced turbidity compared to a corresponding method in which no detectable arginine or arginine derivative is used in a wash solution.

In some embodiments of this aspect, the pH of the neutralized eluate is between about 6.5 and about 8.2. In certain embodiments, the wash solution comprises arginine or an arginine derivative in a concentration greater than 0.5 M and less than about 1.0 M. In some embodiments, the pH of the wash solution is greater than 5.0 and less than about 8.0. In some embodiments of this aspect, the method does not comprise anionic upstream adsorptive filtration. In certain embodiments, the product in the eluate is further purified and/or formulated for therapeutic use.

In another aspect, a method for reducing turbidity and impurities in an eluate comprising a product is provided. The method comprises providing a load fluid comprising the product and one or more impurities, and contacting the load fluid with a medium, wherein the medium can bind the product under conditions suitable for binding the product, thereby providing a bound medium. The method further comprises contacting the bound medium with one or more wash solutions, wherein at least one wash solution comprises arginine or an arginine derivative, thereby providing a washed medium. The method further comprises contacting the washed medium with an elution solution under conditions suitable for eluting the product, thereby generating an eluate comprising the product, and neutralizing the. The method provides an eluate, wherein the ratio of the product to at least one impurity in the eluate is increased and wherein the eluate has reduced turbidity compared to a corresponding method in which no detectable arginine or arginine derivative is used in a wash solution.

In some embodiments of this aspect, the pH of the neutralized eluate is between about 6.5 and about 8.2. In certain embodiments, the wash solution comprises arginine or an arginine derivative in a concentration greater than 0.5 M and less than about 1.0 M. In some embodiments, the pH of the wash solution is greater than 5.0 and less than about 8.0. In some embodiments of this aspect, the method does not comprise anionic upstream adsorptive filtration. In certain embodiments, the product in the eluate is further purified and/or formulated for therapeutic use. The invention also relates to various methods and products as recited in the claims appended hereto.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

DETAILED DESCRIPTION OF THE INVENTION

Figure 1:
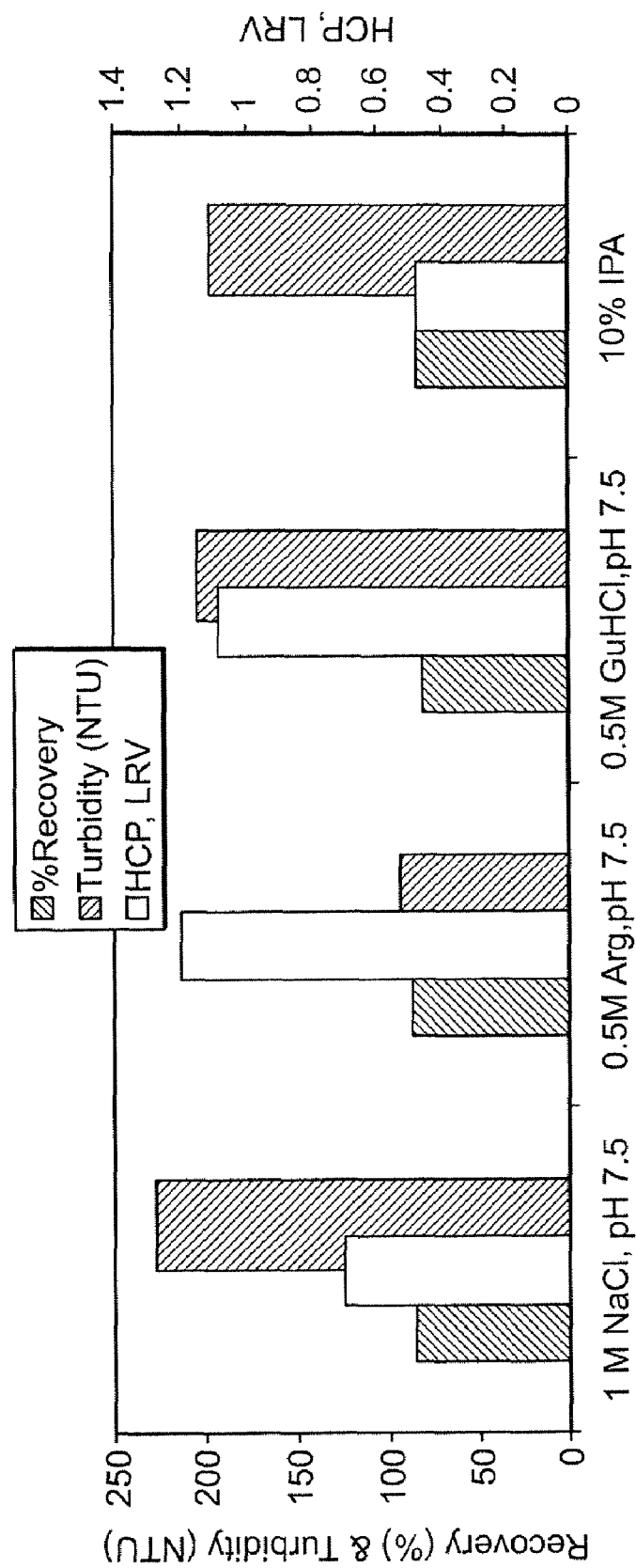
FIG. 1 is a bar graph depicting the results of experiments assaying the percent recovery (%), turbidity, HCP ("host cell proteins") and LRV ("log removal value") of GDF-8 mAb-1 following a Protein A column step.

The present invention provides methods for purifying and recovering products from a load fluid containing one or more impurities using a procedure including an arginine wash or wash with an arginine derivative. The invention can be applied to the large-scale preparation of proteins for therapeutic and/or diagnostic purposes.

A. DEFINITIONS

In order that the present invention may be more readily understood, certain terms as used herein are defined. Additional definitions are set forth throughout the detailed description.

The term "product" refers to a molecule produced by human or by a natural process. A "product" can include, without limitation, a protein, e.g., a therapeutic protein, including an Igfusion protein including, Fc-containing proteins. Other proteins include an immunoconjugate, a cytokine, an interleukin, a hormone, a therapeutic enzyme, a virus, a therapeutic serum, a toxin, an antitoxin, a vaccine, a blood component or derivative, or any analogous product. The protein can be a secreted protein. The protein can be, e.g., an antibody, an antigen-binding fragment of an antibody, a soluble receptor, a receptor fusion, a cytokine, a growth factor, an enzyme, or a clotting factor. As used herein, the terms "product" and "protein of interest" are used interchangeably.

The term "protein" as used herein refers to one or more polypeptides that can function as a unit. The term "polypeptide" as used herein refers to a sequential chain of amino acids linked together via peptide bonds.

A therapeutic protein can be, for example, a secreted protein. Therapeutic proteins include antibodies, antigen-binding fragments of antibodies, soluble receptors, receptor fusions, cytokines, growth factors, enzymes, or clotting factors, some of which are described in more detail herein below. The above list of proteins is merely exemplary in nature, and is not intended to be a limiting recitation. One of ordinary skill in the art will understand that any protein may be used in accordance with the present invention and will be able to select the particular protein to be produced based as needed. The term "conditioned culture medium" as used herein refers to the supernatant that is generated from the removal of cells and cellular debris by a separation method, such as centrifugation and/or microfiltration, from cell culture medium that has been exposed to host cells, which may secrete desired recombinant polypeptide(s) of interest. Conditioned medium can contain, e.g., the secreted recombinant polypeptide, or product of interest; selected nutrients (e.g. vitamins, amino acids, cofactors, and minerals); additional growth factors/supplements including insulin; and additional exogenous, or host cell proteins and impurities. The term conditioned culture medium includes clarified conditioned medium, filtered conditioned medium, and conditioned cell culture medium.

The term "load fluid" refers to a liquid containing the product to be isolated and one or more impurities. A load fluid contacts a medium (e.g., is passed through a medium) under the operating conditions of the invention described below.

The term "impurity" refers to any foreign or undesirable molecule that is present in a solution such as a load fluid. An impurity can be a biological macromolecule such as a DNA, an RNA, or a protein, other than the protein of interest being purified, that is also present in a sample of the protein of interest being purified. Impurities include, for example, undesirable protein variants, such as aggregated proteins, misfolded proteins, underdisulfide-bonded proteins, high molecular weight species, low molecular weight species and fragments, and deamidated species; other proteins from host cells that secrete the protein being purified, host cell DNA, components from the cell culture medium, molecules that are part of an absorbent used for affinity chromatography that leach into a sample during prior purification steps, for example, Protein A; an endotoxin; a nucleic acid; a virus, or a fragment of any of the forgoing.

The term "medium" refers to an affinity matrix or resin that can undergo a ligand-biomacromolecule interaction with a product to be isolated during a macromolecular separation process. The medium can be, without limitation, a Protein A chromatography column or a Protein G chromatography column.

The term "bound medium" refers to a medium bound with a product to be isolated and also bound with one or more impurities. A bound medium can be created by passing a load fluid through a medium under conditions suitable for binding the product.

The term "washed medium" refers to a bound medium that is washed by one or more wash solutions, and at least one wash solution contains arginine or an arginine derivative. A washed medium can be created by contacting a bound medium with one or more wash solutions, and at least one wash solution includes arginine or an arginine derivative. In the washed medium, the purity of the product to be isolated is generally increased relative to the load fluid in bound medium (i.e., the ratio of the product to one or more impurities is increased).

The term "bind-elute mode" refers to a product preparation technique in which at least one product contained in a load fluid binds to a medium (e.g., a chromatographic resin).

The term "antibody" refers to any immunoglobulin or fragment thereof, and encompasses any polypeptide comprising an antigen-binding site. The term includes, but is not limited to, polyclonal, monoclonal, monospecific, polyspecific, non-specific, humanized, human, single-chain, chimeric, synthetic, recombinant, hybrid, mutated, grafted, and in vitro generated antibodies. Antibody fragments include Fab, F(ab')$_2$, Fv, scFv, Fd, dAb, which may retain antigen-binding function. Typically, such fragments include an antigen-binding domain.

The term "IL-13" refers to interleukin-13, including full-length unprocessed precursor form of IL-13, as well as the mature forms resulting from post-translational cleavage. Interleukin-13 (IL-13) is a previously characterized cytokine secreted by T lymphocytes and mast cells (McKenzie et al. (1993) *Proc. Natl. Acad. Sci. USA* 90:3735-39; Bost et al. (1996) *Immunology* 87:663-41). The term also refers to any fragments and variants of IL-13 that maintain at least some biological activities associated with mature IL-13, including sequences that have been modified. The term "IL-13" includes human IL-13, as well as other IL-13 derived from vertebrate species. Several pending applications disclose antibodies against human and monkey IL-13, IL-13 peptides, vectors and host cells producing the same that can be used in the methods described herein, for example, U.S. Application Publication Nos. 2006/0063228A and 2006/0073148. The contents of all of these publications are incorporated by reference herein in their entirety.

IL-13 shares several biological activities with IL-4. For example, either IL-4 or IL-13 can cause IgE isotype switching in B cells (Tomkinson et al. (2001) *J. Immunol.* 166:5792-5800). Additionally, increased levels of cell surface CD23 and serum CD23 (sCD23) have been reported in asthmatic patients (Sanchez-Guererro et al. (1994) *Allergy* 49:587-92; DiLorenzo et al. (1999) *Allergy Asthma Proc.* 20:119-25). In addition, either IL-4 or IL-13 can upregulate the expression of MHC class II and the low-affinity IgE receptor (CD23) on B cells and monocytes, which results in enhanced antigen presentation and regulated macrophage function (Tomkinson et al., supra). These observations indicate that IL-13 plays an important role in the development of airway eosinophilia and airway hyperresponsiveness (AHR) (Tomkinson et al., supra; Wills-Karp et al. (1998) *Science* 282:2258-61). Accordingly, inhibition of IL-13 can be useful in ameliorating the pathology of certain inflammatory and/or allergic conditions, including, but not limited to, respiratory disorders, e.g., asthma; chronic obstructive pulmonary disease (COPD); other conditions involving airway inflammation, eosinophilia, fibrosis and excess mucus production, e.g., cystic fibrosis and pulmonary fibrosis; atopic disorders, e.g., atopic dermatitis, urticaria, eczema, allergic rhinitis; inflammatory and/or autoimmune conditions of, the skin (e.g., atopic dermatitis), gastrointestinal organs (e.g., inflammatory bowel diseases (IBD), such as ulcerative colitis and/or Crohn's disease), liver (e.g., cirrhosis, hepatocellular carcinoma); scleroderma; tumors or cancers (e.g., soft tissue or solid tumors), such as leukemia, glioblastoma, and lymphoma, e.g., Hodgkin's lymphoma; viral infections (e.g., from HTLV-1); fibrosis of other organs, e.g., fibrosis of the liver, (e.g., fibrosis caused by a hepatitis B and/or C virus).

The term "GDF-8" refers to Growth and Differentiation Factor-8 and factors that are structurally or functionally related to GDF-8, for example, BMP-11 and other factors belonging to the TGF-β superfamily. The term refers to the full-length unprocessed precursor form of GDF-8, as well as the mature and propeptide forms resulting from post-translational cleavage. The term also refers to any fragments and variants of GDF-8 that maintain at least some biological activities associated with mature GDF-8, including sequences that have been modified. The amino acid sequences of human GDF-8, as well as GDF-8 of other vertebrate species (including murine, baboon, bovine, and chicken) are disclosed, e.g., US 2004-0142382, US 2002-0157125, and McPherron et al. (1997) *Proc. Nat. Acad. Sci. U.S.A.*, 94:12457-12461, the contents of all of which are hereby incorporated by reference in their entirety. Examples of neutralizing antibodies against GDF-8 are disclosed in, e.g., US 2004-0142382, and may be used to treat or prevent conditions in which an increase in muscle tissue or bone density is desirable. Exemplary disease and disorders include muscle and neuromuscular disorders such as muscular dystrophy (including Duchenne's muscular dystrophy); amyotrophic lateral sclerosis; muscle atrophy; organ atrophy; frailty; tunnel syndrome; congestive obstructive pulmonary disease; sarcopenia, cachexia, and other muscle wasting syndromes; adipose tissue disorders (e.g., obesity); type 2 diabetes; impaired glucose tolerance; metabolic syndromes (e.g., syndrome X); insulin resistance induced by trauma such as burns or nitrogen imbalance; and bone degenerative diseases (e.g., osteoarthritis and osteoporosis).

GDF-8, also known as myostatin, is a secreted protein and is a member of the transforming growth factor-beta (TGF-β) superfamily of structurally related growth factors, all of which possess physiologically important growth-regulatory and morphogenetic properties (Kingsley et al. (1994) *Genes Dev.,* 8: 133-146; Hoodless et al. (1998) *Curr. Topics Microbiol. Immunol.,* 228: 235-272). Similarly to TGF-β, human GDF-8 is synthesized as a 375 amino acid long precursor protein. The precursor GDF-8 protein forms a homodimer. During processing, the amino-terminal propeptide is cleaved off at Arg-266. The cleaved propeptide, known as the "latency-associated peptide" (LAP), may remain noncovalently bound to the homodimer, thereby inactivating the complex (Miyazono et al. (1988) *J. Biol. Chem.* 263: 6407-6415; Wakefield et al. (1988) *J. Biol. Chem.* 263: 7646-7654; Brown et al. (1990) *Growth Factors,* 3: 35-43; and Thies et al. (2001) *Growth Factors,* 18: 251-259). The complex of mature GDF-8 with propeptide is commonly referred to as the "small latent complex" (Gentry et al. (1990) *Biochemistry,* 29: 6851-6857; Derynck et al. (1995) *Nature,* 316: 701-705; and Massague (1990) *Ann. Rev. Cell Biol.,* 12: 597-641). Other proteins are also known to bind to mature GDF-8 and inhibit its biological activity. Such inhibitory proteins include follistatin and follistatin-related proteins (Gamer et al. (1999) *Dev. Biol.,* 208: 222-232).

The term "RAGE" refers to the Receptor for Advanced Glycation End products. RAGE is a multi-ligand cell surface member of the immunoglobulin super-family. RAGE consists of an extracellular domain, a single membrane-spanning domain, and a cytosolic tail. The extracellular domain of the receptor consists of one V-type immunoglobulin domain followed by two C-type immunoglobulin domains. RAGE also exists in a soluble form (sRAGE). RAGE is a pattern-recognition receptor that binds several different classes of endogenous molecules leading to various cellular responses, including cytokine secretion, increased cellular oxidant stress, neurite outgrowth and cell migration. The ligands of RAGE include advanced glycation end products (AGEs), which form in prolonged hyperglycemic states. In addition to AGEs, known ligands of RAGE include proteins having β-sheet fibrils that are characteristic of amyloid deposits and pro-inflammatory mediators, including S100/calgranulins (e.g., S100A12, S100B, S100A8-A9), serum amyloid (SAA) (fibrillar form), beta-Amyloid protein (A-Beta), and high mobility group box-1 chromosomal protein 1 (HMGB1, also known as amphoterin). RAGE is expressed by many cell types, e.g., endothelial and smooth muscle cells, macrophages and lymphocytes, and in many different tissues, including lung, heart, kidney, skeletal muscle and brain. Expression is increased in chronic inflammatory states such as rheumatoid arthritis and diabetic nephropathy. Although its physiologic function is unclear, RAGE is involved in the inflammatory response and may have a role in diverse developmental processes, including myoblast differentiation and neural development. A number of significant human disorders are associated with an increased production of ligands for RAGE or with increased production of RAGE itself. These disorders include, for example, many chronic inflammatory diseases, including rheumatoid and psoriatic arthritis and intestinal bowel disease, cancers, diabetes and diabetic nephropathy, amyloidoses, cardiovascular diseases and sepsis. For example, one of the ligands for RAGE, HMGB-1, has been shown to be a late mediator of lethality in two models of murine sepsis, and interaction between RAGE and ligands such as HMGB1 is believed to play an important role in the pathogenesis of sepsis and other inflammatory diseases.

The term "A-Beta" refers to the principal constituent of amyloid plaques within the brain. A-Beta peptide is a 4-kDa internal fragment of 39-43 amino acids of a larger transmembrane glycoprotein named amyloid precursor protein (APP). As a result of proteolytic processing of APP by different secretase enzymes, A-Beta is primarily found in both a short form, 40 amino acids in length, and a long form, ranging from 42-43 amino acids in length. Part of the hydrophobic transmembrane domain of APP is found at the carboxy end of A-Beta, and may account for the ability of A-Beta to aggregate into plaques, particularly in the case of the long form. Accumulation of amyloid plaques in the brain eventually leads to neuronal cell death. The physical symptoms associated with this type of neural deterioration characterize Alzheimer's disease (AD). The accumulation of amyloid plaques within the brain is also associated with Down's syndrome and other cognitive disorders.

Several mutations within the APP protein have been correlated with the presence of AD (see, e.g., Goate et al., Nature 349:704, 1991 (valine717 to isoleucine); Chartier Harlan et al. Nature 353:844, 1991 (valine717 to glycine); Murrell et al., Science 254:97, 1991 (valine717 to phenylalanine); Mullan et al., Nature Genet. 1:345, 1992 (a double mutation changing lysine595-methionine596 to asparagine595-leucine596), each of which is incorporated herein by reference in its entirety). Such mutations are thought to cause AD by increased or altered processing of APP to A-Beta, particularly processing of APP to increased amounts of the long form of A-Beta (i.e., A-Beta1-42 and A-Beta1-43). Mutations in other genes, such as the presenilin genes, PS1 and PS2, are thought indirectly to affect processing of APP to generate increased amounts of long form A-Beta (see Hardy, TINS 20: 154, 1997, incorporated herein by reference in its entirety). In certain embodiments, anti-A-Beta antibodies are purified in accordance with the present invention.

As used herein, the term "IL-22" refers to interleukin-22, including full-length unprocessed precursor form of IL-22, as well as the mature forms resulting from post-translational cleavage. The term also refers to any fragments and variants of IL-22 that maintain at least some biological activities associated with mature IL-22, including sequences that have been modified. The term "IL-22" includes human IL-22, as well as other vertebrate species. The amino acid and nucleotide sequences of human and rodent IL-22, as well as antibodies against IL-22 are disclosed in, for example, U.S. Application Publication Nos. 2003-0157106, 2005-0153400, 2005-0042220 and 2005-0158760, and U.S. Pat. No. 6,939,545. The contents of all of these publications are incorporated by reference herein in their entirety.

Interleukin-22 (IL-22) is a previously characterized class II cytokine that shows sequence homology to IL-10. Its expression is up-regulated in T cells by IL-9 or Concanavalin A (ConA) (Dumoutier L. et al. (2000) *Proc Natl Acad Sci USA* 97(18): 10144-9). Studies have shown that expression of IL-22 mRNA is induced in vivo in response to lipopolysaccharide (LPS) administration, and that IL-22 modulates parameters indicative of an acute phase response (Dumoutier L. et al. (2000) supra; Pittman D. et al. (2001) *Genes and Immunity* 2:172), and that a reduction of IL-22 activity by using a neutralizing anti-IL-22 antibody ameliorates inflammatory symptoms in a mouse collagen-induced arthritis (CIA) model. Thus, IL-22 antagonists, e.g., neutralizing anti-IL-22 antibodies and fragments thereof, can be used to induce immune suppression in vivo, for examples, for treating autoimmune disorders (e.g., arthritic disorders such as rheumatoid arthritis); respiratory disorders (e.g., asthma, chronic obstructive pulmonary disease (COPD)); inflammatory conditions of, e.g., the skin (e.g., psoriasis), cardiovascular system (e.g., atherosclerosis), nervous system (e.g., Alzheimer's disease), kidneys (e.g., nephritis), liver (e.g., hepatitis) and pancreas (e.g., pancreatitis).

The term "host cell proteins (HCP)" refers to non-product proteins produced by a host cell during cell culture or fermentation. Accordingly, in some embodiments, an eluate containing a product has HCPs present in less than 100 parts per million (ppm) HCPs (e.g., less than about 50 ppm, or less than about 20 ppm). HCP composition is extremely heterogeneous and dependent on the protein product and purification procedure used. Prior to any marketing approval of a biological product for therapeutic use, the level of contaminating proteins (such as HCPs) in the product must be quantitatively measured according to the ICH and FDA guidelines.

The term "column effluent" refers to the liquid exiting a medium or column during a load cycle, or in the period during which a load is being applied.

B. DETAILED DESCRIPTION OF THE INVENTION

The present invention provides methods for purifying and recovering products from a load fluid containing one or more impurities using a procedure that includes washing a bound medium with arginine or an arginine derivative. In a preferred embodiment, the medium is a Protein A chromatography column.

In one embodiment, a product is a protein, e.g., a therapeutic protein, including peptide antibodies. In other embodiments, the product is a secreted protein; a fusion protein, e.g., a receptor fusion protein or an Ig-fusion protein, including Fc-fusion proteins; a soluble receptor; a growth factor; an enzyme; a clotting factor; an Fc-containing protein; an immunoconjugate; a cytokine; an interleukin; a hormone; or a therapeutic enzyme.

In further embodiments of the invention, the product is protein, e.g., an antibody, that has a $C_H2/C_H3$ region and therefore is amenable to purification by Protein A chromatography. The term "$C_H2/C_H3$ region" refers to those amino acid residues in the Fc region of an immunoglobulin molecule that interact with Protein A. In some embodiments, the $C_H2/C_H3$ region contains an intact $C_H^2$ region followed by an intact $C_H^3$ region. In other embodiments, the $C_H2/C_H3$ region contains an Fc region of an immunoglobulin. Examples of $C_H2/C_H3$ region-containing proteins include antibodies, immunoadhesins and fusion proteins that include a protein of interest fused to, or conjugated with, a $C_H2/C_H3$ region.

In certain embodiments, at least one impurity is bound to the medium and/or the product when the load fluid is loaded to the medium, and at least one wash solution containing arginine or an arginine derivative is used to remove the impurity that is bound to the medium and/or the product.

The protein can be a secreted protein. The protein can be an antibody, an antigen-binding fragment of an antibody, a soluble receptor, a receptor fusion, a cytokine, a growth factor, an enzyme, or a clotting factor.

In some embodiments of the invention, the protein purified using the method of the invention is an antibody or an antigen-binding fragment thereof. As used herein, the term "antibody" includes a protein comprising at least one, and typically two, VH domains or portions thereof, and/or at least one, and typically two, VL domains or portions thereof. In certain embodiments, the antibody is a tetramer of two heavy immunoglobulin chains and two light immunoglobulin chains, wherein the heavy and light immunoglobulin chains are interconnected by, e.g., disulfide bonds. The antibodies, or a portion thereof, can be obtained from any origin, including, but not limited to, rodent, primate (e.g., human and non-human primate), camelid, shark as well as recombinantly produced, e.g., chimeric, humanized, and/or in vitro generated, e.g., by methods well known to those of skill in the art.

Examples of binding fragments encompassed within the term "antigen-binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment, which consists of a VH domain; (vi) a camelid or camelized variable domain, e.g., a VHH domain; (vii) a single chain Fv (scFv); (viii) a bispecific antibody; and (ix) one or more antigen binding fragments of an immunoglobulin fused to an Fc region. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) *Science* 242:423-26; Huston et al. (1988) *Proc. Natl. Acad. Sci. U.S.A.* 85:5879-83). Such single chain antibodies are also intended to be encompassed within the term "antigen-binding fragment" of an antibody. These antibody fragments are obtained using conventional techniques known to those skilled in the art, and the fragments are evaluated for function in the same manner as are intact antibodies.

In some embodiments, the term "antigen-binding fragment" encompasses single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, goat, rabbit, cow and shark. According to one aspect of the invention, a single domain antibody as used herein is a naturally occurring single domain antibody known as heavy chain antibody devoid of light chains. Such single domain antibodies are disclosed in WO 9404678 for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

An antigen-binding fragment can, optionally, further include a moiety that enhances one or more of, e.g., stability, effector cell function or complement fixation. For example, the antigen-binding fragment can further include a pegylated moiety, albumin, or a heavy and/or a light chain constant region.

In addition, the methods of the present invention can be used to purify small modular immunopharmaceutical (SMIP™) drugs (Trubion Pharmaceuticals, Seattle, Wash.). SMIPs are single-chain polypeptides composed of a binding domain for a cognate structure such as an antigen, a counter-receptor or the like, a hinge-region polypeptide having either one or no cysteine residues, and immunoglobulin CH2 and CH3 domains (see also www.trubion.com). SMIPs and their uses and applications are disclosed in, e.g., U.S. Published Patent Application. Nos. 2003/0118592, 2003/0133939, 2004/0058445, 2005/0136049, 2005/0175614, 2005/0180970, 2005/0186216, 2005/0202012, 2005/0202023, 2005/0202028, 2005/0202534, and 2005/0238646, and related patent family members thereof, all of which are hereby incorporated by reference herein in their entireties.

Other than "bispecific" or "bifunctional" antibodies, an antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

In embodiments where the protein is an antibody or a fragment thereof, it can include at least one, or two full-length heavy chains, and at least one, or two light chains. Alternatively, the antibodies or fragments thereof can include only an antigen-binding fragment (e.g., an Fab, F(ab')$_2$, Fv or a single chain Fv fragment). The antibody or fragment thereof can be a monoclonal or single specificity antibody. The antibody or fragment thereof can also be a human, humanized, chimeric, CDR-grafted, or in vitro generated antibody. In yet other embodiments, the antibody has a heavy chain constant region chosen from, e.g., IgG1, IgG2, IgG3, or IgG4. In another embodiment, the antibody has a light chain chosen from, e.g., kappa or lambda. In one embodiment, the constant region is altered, e.g., mutated, to modify the properties of the antibody (e.g., to increase or decrease one or more of: Fc receptor binding, antibody glycosylation, the number of cysteine residues, effector cell function, or complement function). Typically, the antibody or fragment thereof specifically binds to a predetermined antigen, e.g., an antigen associated with a disorder, e.g., a neurodegenerative, metabolic, inflammatory, autoimmune and/or a malignant disorder. Exemplary antibodies that can be separated by the methods of the invention include, but are not limited to, antibodies against RAGE, A-Beta peptide, interleukin-13 (IL-13), interleukin-22 (IL-22), 5T4, and growth and differentiation factor-8 (GDF-8).

The antibody preparations used with methods described herein can be from a number of sources including, but not limited to, serum of an immunized animal, ascites fluid, hybridoma or myeloma supernatants, conditioned culture medium derived from culturing a recombinant cell line that expresses the antibody molecule, or from a cell extract of antibody-producing cells. In one embodiment of the invention, the product is an antibody from conditioned culture medium of an antibody-producing recombinant cell line. Although there can be some variation from cell line to cell line and among the various antibody products, based on the disclosure herein, it is well within the purview of one of ordinary skill in this art to adapt the invention herein to a particular combination of antibody protein and producing cell line.

In certain embodiments, at least one impurity is bound to the medium and/or the product when the load fluid is loaded to the medium, and at least one wash solution containing arginine or an arginine derivative is used to remove the impurity that is bound to the medium and/or the product. In one embodiment of the invention, the purified product contains less than 60% impurities (e.g., host cell proteins), in one embodiment, 40% impurities, in one embodiment, 20% impurities, in one embodiment, 10% impurities, in one embodiment, 5% impurities, in one embodiment, less than 3% impurities, and in another embodiment, less than 1% impurities. Impurities include, but are not limited to, undesirable protein variants, such as aggregated proteins, high molecular weight species, low molecular weight species and fragments, and deamidated species; other proteins from host cells that secrete the protein being purified; host cell DNA; components from the cell culture medium, molecules that are part of an absorbent used for affinity chromatography that leach into a sample during prior purification steps, for example, Protein A and Protein G; an endotoxin; a nucleic acid; a virus, or a fragment of any of the forgoing.

The medium used in a method described herein is, for example, an affinity chromatography column, a hydrophobic interaction chromatography column, an immobilized metal affinity chromatography column, a size exclusion chromatography column, a diafiltration, ultrafiltration, viral removal filtration, and/or ion exchange chromatography column, a Protein A chromatography column or a Protein G chromatography column. A Protein A chromatography column can be, for example, PROSEP-A™ (Millipore, U.K.), Protein A Sepharose FAST FLOW™ (GE Healthcare, Piscataway, N.J.), TOYOPEARL™ 650M Protein A (TosoHass Co., Philadelphia, Pa.), or MabSelect™ column (GE Healthcare, Piscataway, N.J.).

Before contacting the medium with a load fluid, it may be necessary to adjust parameters such as pH, ionic strength, and temperature and in some instances the addition of substances of different kinds. Thus, it is an optional step to perform an equilibration of the medium by washing it with a solution (e.g., a buffer for adjusting pH, ionic strength, etc., or for the introduction of a detergent) bringing the necessary characteristics for binding and purification of the product.

In one embodiment of the invention, a Protein A column is equilibrated and washed with a wash solution containing arginine or an arginine derivative, thereby bringing the necessary characteristics for purifying the product. In one embodiment of the invention, the Protein A column may be equilibrated using a solution containing a salt, e.g., about 100 mM to about 150 mM NaPO$_4$, about 100 mM to about 150 mM sodium acetate, and about 100 mM to about 150 mM NaCl. The pH of the equilibration buffer may range from about 6.0 to about 8.0. In one embodiment, the pH of the equilibration buffer is about 7.5. The equilibration buffer may contain about 10 mM to about 50 mM Tris. In another embodiment, the buffer may contain about 20 mM Tris. After contacting the medium (e.g., a Protein A column) with the load fluid, the bound medium is washed. In accordance with the invention, the wash solution used in the method described herein contains arginine or an arginine derivative. The arginine derivative can be, but is not limited to, acetyl arginine, agmatine, arginic acid, N-alpha-butyroyl-L-arginine, or N-alpha-pyvaloyl arginine.

The concentration of arginine or arginine derivative in the wash solution is between about 0.1 M and about 2.0 M (e.g., 0.1 M, 0.4 M, 0.5 M, 1.0 M, 1.5 M, or 2.0 M), or between about 0.5 M and about 1.0 M (e.g, 0.5 M, 0.6 M, 0.7 M, 0.8 M, 0.9 M, or 1.0 M). In certain embodiments, the concentration of arginine or arginine derivative in the wash solution is about 0.1 M, 0.2 M, 0.3 M, 0.4 M, 0.5 M, 0.6 M, 0.7 M, 0.8 M, or 0.9 M. In certain embodiments, the concentration of arginine or arginine derivative in the wash solution is about 1.1 M, 1.2 M, 1.3 M, 1.4 M, 1.5 M, 1.6 M, 1.7 M, 1.8 M, 1.9 M, or 2.0 M. In certain embodiments, the concentration of arginine or arginine derivative in the wash solution is greater than about 0.5 M and less than about 2.0 M (e.g., 0.55 M, 0.75 M, 1.0 M, 1.25 M, 1.5 M, or 1.75 M, or 2.0 M), or greater than about 0.5 M and less than about 1.0 M (e.g., 0.55 M, 0.75 M, or 1.0 M). In one embodiment, the concentration of arginine is not 1 M. In some embodiments, the concentration of arginine or arginine derivative in the wash solution is greater than 1M. In some embodiments, the concentration of arginine or arginine derivative in the wash solution is less than 1M. In further embodiments, the wash solution may contain about 0.1 M to about 0.9 M arginine or arginine derivative. In certain embodiments, the concentration of arginine or arginine derivative can be about 0.2 M to about 0.8 M, about 0.3 M to about 0.7 M, or about 0.4 M to about 0.6 M. In further embodiments, the wash solution may contain about 1.1 M to about 3.0 M, or about 1.1 M to about 2.0 M arginine or arginine derivatives. In certain embodiments, the concentration of arginine or arginine derivative is about 1.2 M to about 2.8 M, about 1.3 M to about 2.6 M, about 1.4 M to about 2.4 M, about 1.5 M to about 2.2 M, about 1.6 M to about 2.0 M, or about 1.8 M to about 2.0 M. In certain embodiments, the concentration of arginine or arginine derivative is about 1.2 M to about 1.9 M, about 1.3 M to about 1.8 M, about 1.4 M to about 1.7 M, or about 1.5 M to about 1.6 M.

The pH of the wash solution is generally between about 4.5 and about 8.0, for example, 4.5, 5.0, 5.5, 6.0, 6.5, 7.0, 7.5 and 8.0. In same cases, the pH of the wash solution is greater than 5.0 and less than about 8.0, for example, 5.5, 6.0, 6.5, 7.0, 7.5 and 8.0. The wash solution may contain 20 mM to 50 mM Tris (e.g., 20 mM, 30 mM, 40 mM or 50 mM). In one embodiment the bound medium is washed with 5 column volumes of the wash solution, followed by an elution step.

In certain embodiments of the invention, the product may be eluted from a washed medium, e.g., a Protein A column. To elute a product from a Protein A column, the washed medium is contacted with an elution buffer. In some embodiments, the elution buffer contains about 15 mM to about 50 mM NaCl. In other embodiments, the elution buffer may contain about 50 mM to about 150 mM arginine or arginine derivatives. In further embodiments, the elution buffer may contain 50 mM to 150 mM glycine. The elution buffer may also contain about 20 mM to about 30 mM HEPES. The elution buffer may also contain about 25 mM to about 50 mM acetic acid. The pH of the elution buffer may range from about 2.0 to about 4.0. In one embodiment, the pH of the elution buffer is about 3.0.

The medium may optionally be cleaned, i.e., stripped and regenerated, after elution of the antibody. This procedure is typically performed regularly to minimize the building up of impurities on the surface of the solid phase and/or to sterilize the matrix to avoid contamination of the product with microorganisms.

Buffer components may be adjusted according to the knowledge of the person of ordinary skill in the art. Sample buffer composition ranges are provided in the Examples below. Not all of the buffers or steps are necessary, but are provided for illustration only. A high throughput screen, as described in the Examples, may be used to efficiently optimize buffer conditions for Protein A column chromatography.

In one embodiment of the method, the eluate includes an isolated product and the purity of the isolated product is increased compared to a corresponding method in which less than about 0.1 M of arginine or arginine derivative is used in a wash solution.

In another embodiment, the eluate includes an isolated product, and the ratio of the product to at least one impurity is increased compared to a corresponding method in which no detectable amount of arginine or arginine derivative is used in a wash solution.

In some cases, the eluate contains a product, and the ratio of the product to host cell protein is increased compared to a corresponding method in which less than about 0.1 M of arginine or arginine derivative is used in a wash solution.

The eluate can include a product and the ratio of the product to host cell protein is increased compared to a corresponding method in which no detectable amount of arginine or arginine derivative is used in a wash solution.

Turbidity provides a measure of insoluble product, insoluble impurities, and insoluble complexes of product and impurities. Turbidity can also be caused by sub-cellular particulates and cell debris. In general, lower turbidity in the eluate is associated with a more desirable quality of the product. Turbidity can be assayed using methods known in the art. For example, nephelometric methods (Baker et al., Trends Biotechnol. 2002 April; 20(4):149-56) or optical density can be used. Optical density is generally assayed by measuring absorbance at a range of about 320 nm to about 650 nm.

In some cases, the turbidity of the eluate is reduced compared to the turbidity of the eluate in a corresponding method in which less than about 0.1 M of arginine or arginine derivative is used in a wash solution. In certain methods, the turbidity of the eluate is reduced compared to a corresponding method in which no detectable amount of arginine or arginine derivative is used in a wash solution.

In certain embodiments, the method of the present invention results in reduced turbidity in an eluate that contains a product. In other embodiments, the method results in reduced turbidity as well as reduced impurities in the eluate that contains the product compared to a corresponding method in which no detectable amount of arginine or arginine derivative is used in a wash solution. In certain embodiments, the method does not include the use of any additional upstream filtration, for example, an anionic upstream adsorptive filtration.

Although the purification method of the present invention can be used alone, it may be used in combination with other purification techniques. In one embodiment, one or more processes can be used, e.g., to prepare a load fluid to reduce the load challenge of the contaminants or impurities while employing the methods described herein. In some cases, one or more processes are used to process the eluate, e.g., to remove contaminants or impurities that are in the eluate.

The present invention also relates to a product prepared according to a method described herein. In general, it will typically be desirable to further isolate and/or purify products isolated according to the present invention and formulate them for pharmaceutical use according to standard methods. For proteins, see for example *Protein Purification Principles and Practice* 2nd Edition, Springer-Verlag, New York, 1987; Higgins, S. J. and Hames, B. D. (eds.), and Deutscher, M. P.,  Simon, M. I., Abelson, J. N. (eds.), *Guide to Protein Purification: Methods in Enzymology* (Methods in Enzymology Series, Vol 182), Academic Press, 1997, incorporated herein by reference. One of ordinary skill in the art will appreciate that the exact techniques used will vary depending on the character of the product. Products of the invention having pharmacologic activity will be useful in the preparation of pharmaceuticals. These may be administered to a subject or may first be formulated for delivery by any available route including, but not limited to parenteral (e.g., intravenous), intradermal, subcutaneous, oral, nasal, bronchial, opthalmic, transdermal (topical), transmucosal, rectal, and vaginal.

A pharmaceutical composition of the product is formulated to be compatible with its intended route of administration according to methods known in the art, see for example, Remington: The Science & Practice of Pharmacy", $19^{th}$ ed., Williams & Williams, (1995), and the "Physician's Desk Reference", $52^{nd}$ ed., Medical Economics, Montvale, N.J. (1998). In some embodiments, the product is formulated using sterile water (e.g., SWFI), buffered saline (e.g., phosphate buffered saline), polyol (e.g., glycerol, propylene glycol, liquid polyethylene glycol), or suitable mixtures thereof.

Non-limiting examples of products that can be recovered using the methods described herein include a protein or a peptide, e.g., an antibody, an antibody fragment, a recombinant protein, a naturally secreted protein, a protein or a peptide that is engineered to be secreted, a non-protein product that is produced by a cell, or a combination of the foregoing products.

EXAMPLES

The invention is further illustrated by the following examples. The examples are provided for illustrative purposes only. They are not to be construed as limiting the scope or content of the invention in any way.

Experiments were conducted to identify methods that are useful for isolation of a product that is produced by a cell bacterium or tissue, in protocols that use an affinity medium as part of the isolation process. In these experiments, MabSelect™ Protein A column was used to bind the product.

Example 1

GDF-8 mAb-1

Comparison of Protein A Wash Buffers for HCP and Turbidity Reduction and Product Recovery The evaluation of various wash solutions was first performed using a high throughput screening (HTS) method. A MabSelect™ Protein A column was initially loaded with conditioned culture media from a Chinese Hamster Ovary ("CHO") cell culture process. The MabSelect™ resin was then slurried and 100 µL of the resin slurry was dispensed into each well of a 96-well microtiter plate. Each well of the microtiter plate was then washed with a test solution under evaluation, and subsequently eluted with a low pH buffer. The elution pool from each well was assayed for peak turbidity by A320 and for product recovery by A280. Based on the results from the HTS experiments, test solutions that produced the highest recovery and lowest turbidity were selected for further testing using small-scale column scouting runs. In the column scouting runs, a MabSelect Protein A column was equilibrated with a buffer containing 10 mM Tris, 100 mM NaCl pH 7.5, and loaded with CHO conditioned culture media containing GDF-8 mAb-1. The column was then flushed with 5 column volumes (CV) of the equilibration buffer, and subsequently washed with 5 CVs of a test solution under evaluation. The bound product was subsequently eluted in a low pH buffer. The neutralized peak turbidity was measured by A320 or by a turbidimeter, product recovery was determined by A280, and the HCP level was determined by an ELISA. The column sizes used for initial evaluation were 0.5 cm or 1.1 cm in diameter with bed heights from 8 to 25 cm. Table 1 summarizes the column operating conditions for all experiments described in Example 1.

TABLE 1

MabSelect ™ Protein A column operating conditions

| Phase of column Operation | Solution Composition | Volume (Column Volumes) | Linear velocity (cm hr$^{-1}$) |
|---|---|---|---|
| Equilibration | 10 mM Tris, 100 mM NaCl, pH 7.5 | 5 | 360/450 |
| Load | conditioned culture medium | NA | 240 |
| Post Load Flush | 10 mM Tris, 100 mM NaCl, pH = 7.5 | 2 | 240 |
| Wash 1 | Variable (see Table 2) | 5 | 300 |
| Pre-Elution Flush | 10 mM Tris, 100 mM NaCl, pH = 7.5 | 5 | 450 |
| Elution | 50 mM NaCl, 100 mM L-arsinine HCl, pH = 3.0 | 6 | 150 |
| Neutralization | 2M HEPES, pH = 8.0 | 5.0% (v/v) addition | — |
| Post Elution Flush | 50 mM Tris, pH = 8.5 | 4 | 450 |
| Strip | 6M guanidine HCl | 2 | 150 |
| Post Strip Flush | 10 mM Tris, 100 mM NaCl, pH = 7.5 | 4 | 150/450 |
| Storage | 16% (v/v) ethanol | 4 | 360 |

For each run, the MabSelect™ Protein A column was equilibrated with 5 column volumes of 10 mM Tris, 100 mM NaCl, pH 7.5 and subsequently loaded to approximately 35 mg product/mL resin. The column was then flushed with 1 column volume of equilibration buffer and 5 column volumes (CV) of the test wash under evaluation (see Table 2). The wash phase was followed by 5 CV flush of 10 mM Tris, 100 mM NaCl, pH 7.5. The bound product was then eluted from the column with 100 mM L-arginine, 50 mM NaCl, pH 3.0. The product pool was subsequently neutralized to pH 7.5 with 2 M HEPES, pH 8.0. The column was stripped with 2 CV of 6 M guanidine HCl. The guanidine was removed from the column with 4 CV of 10 mM Tris, 100 mM NaCl, pH 7.5 before being stored in 16% ethanol (4 CV). All column operations were performed at room temperature.

The various wash solutions evaluated for HCP and peak pool turbidity reduction are listed in Table 2. Severe precipitation and product loss was observed in the Protein A elution pool when the control 1M NaCl wash solution was used (FIG. 1). In addition, the HCP clearance across the Protein A column step was less than 1 log$_{10}$. Compared to alternate wash solutions such as 10% isopropanol (IPA), 0.5 M Guanidine-HCl (GuHCl), or 2 M Tris-HCl, the arginine wash was more effective in reducing HCP and elution pool turbidity while maintaining good product recovery (FIG. 1).

TABLE 2

List of wash solutions evaluated

| No. | Solution Composition |
|---|---|
| 1 | 1 M NaCl, 20 mM Tris, pH 7.5 |
| 2 | 0.5 M arginine, 20 mM Tris, pH 7.5 |
| 3 | 0.5 M GuHCl, 20 mM Tris, pH 7.5 |
| 4 | 10% IPA, 20 mM Tris, pH 7.5 |
| 5 | 1 M arginine 20 mM Tris, pH 7.5 |
| 6 | 1 M arginine, 20 mM sodium acetate, pH 5.0 |
| 7 | 2 M Tris, pH 7.5 |

Example 2

GDF-8 mAb-2

Comparison of Protein A Wash Buffers for HCP and Turbidity Reduction and Product Recovery The conditioned culture medium from a CHO cell culture process containing GDF-8 mAb-2 was purified at small scale using a MabSelect™ Protein A column. Column sizes used for initial evaluation were 0.5 cm or 1.1 cm in diameter with bed heights from 8 cm to 25 cm. The Protein A operating conditions used for GDF-8 mAB-2 purification, as well as the wash solutions evaluated for HCP and peak pool turbidity reduction were the same as those used in Example 1 (refer to Table 2 for the test solutions evaluated).

Figure 2:
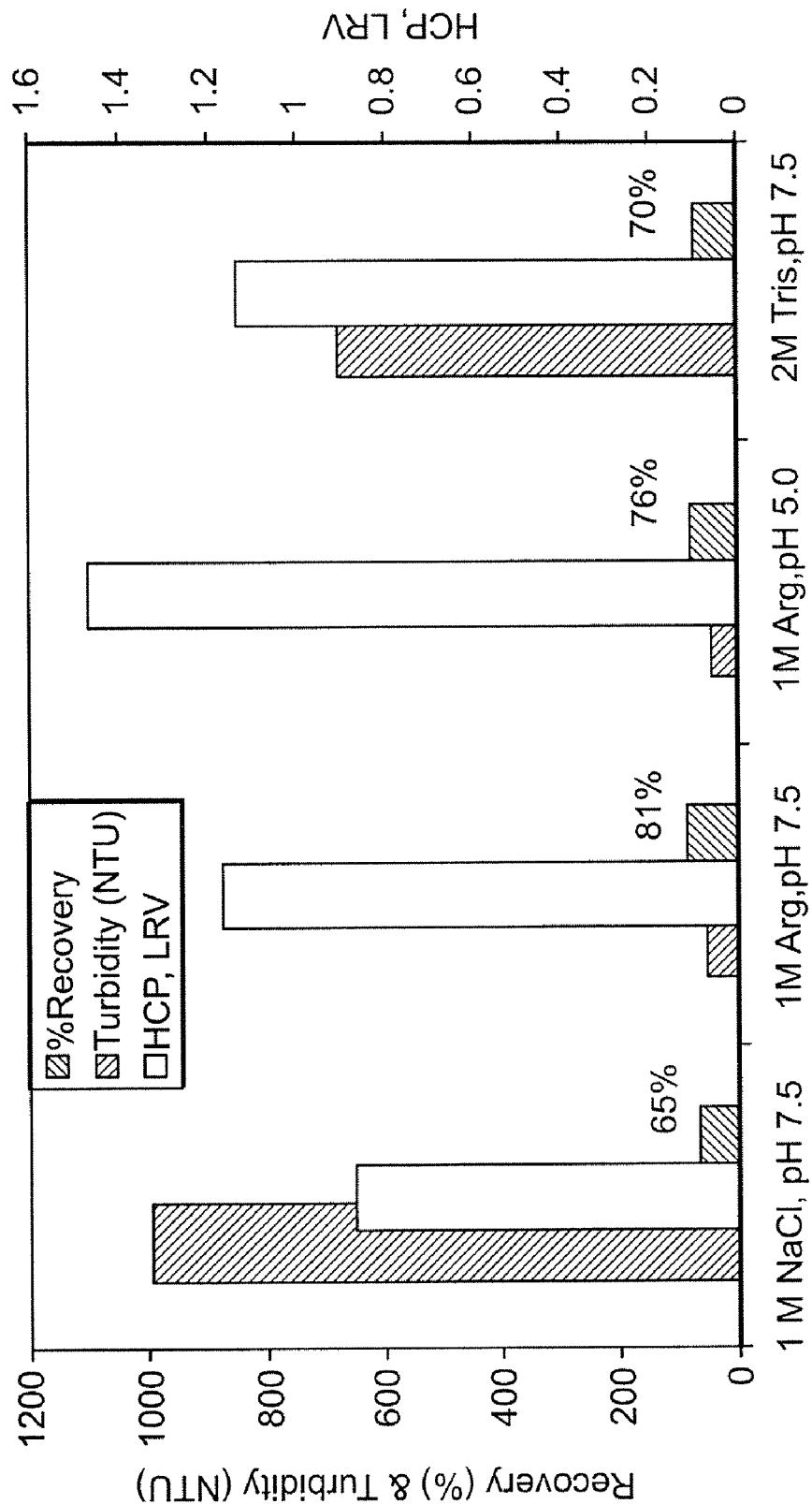
FIG. 2 is a bar graph depicting the results of experiments assaying the percent recovery (%), turbidity, HCP and LRV of GDF-8 mAb-2 following a Protein A column step.

Severe precipitation and product loss was observed in the Protein A elution pool when the control 1M NaCl wash solution was used (FIG. 2). In addition, the HCP clearance across the Protein A column step was less than 1 log$_{10}$. Compared to alternate wash solutions such as 10% isopropanol, 0.5 M Guanidine-HCl (GuHCl), or 2 M Tris-HCl, an arginine wash was more effective in removing HCP and reducing elution pool turbidity while maintaining >75% product recovery (FIG. 2).

Example 3

IL-13 mAb-1

Comparison of Protein A Wash Buffers for HCP and Turbidity Reduction and Product Recovery The evaluation of several wash solutions for turbidity and HCP reduction across the Protein A column step was initially performed using a high throughput screening (HTS) method. A 25 mL column was packed with MabSelect™ resin and loaded with CHO cell conditioned culture media to a final load challenge of 25 mg of IL-13 mAb-1 per mL of resin. The resin was then slurried and 100 µL of the resin slurry was dispensed into each well of a 96-well microtiter plate. Each well of the microtiter plate was then washed with the test solution under evaluation, and the bound product was eluted with 50 mM glycine, 35 mM NaCl, pH 3.0. Table 3 lists all wash solutions evaluated in this study. The elution pool from each well was measured by A320 for peak turbidity and A280 for product recovery.

TABLE 3

Wash solutions evaluated in HTS Screen#1

| Wash Solution | pH | Concentration |
|---|---|---|
| NaCl - Control | 7.5 | 0.15-3.5 M |
| Tween 80 with 150 mM NaCl | 7.5 | 0.05-1.0% |
| Guanidine HCl | 7.5 | 0.1-2.0 M |
| CTAB* | 7.5 | 0.1-1.0% |
| Isopropyl Alcohol (IPA) | 7.5 | 1.0-10.0% |
| Sodium Dodecyl Sulfate (SDS) | 7.5 | 0.05-0.7% |
| Propylene Glycol | 7.5 | 5.0-40.0% |
| Propylene Glycol (low pH) | 5.0 | 2.0-20.0% |
| Propylene Glycol (low pH) | 6.0 | 5.0-30.0% |
| Tween 80 with 0.5M NaCl | 7.5 | 0.05-1.0% |
| CHAPS** | 7.5 | 0.05-1.0% |
| Urea | 7.5 | 0.1-2.0 M |
| Sodium Sulfate | 7.5 | 0.1-0.8 M |
| Sucrose | 7.5 | 1.0-10.0% |
| Glycine | 7.5 | 0.1-1.0 M |
| Glycerol | 7.5 | 1.0-10.0% |
| CaCl$_2$ | 7.5 | 0.25-2.5 M |
| CaCl$_2$ (low pH) | 6.0 | 0.1-1.75 M |
| CaCl$_2$ (low pH) | 5.0 | 0.1-1.75 M |
| Arginine | 7.5 | 0.1-1.0 M |
| Arginine (low pH) | 6.0 | 0.1-1.0 M |
| Arginine (low pH) | 5.0 | 0.1-1.0 M |
| Tris | 7.5 | 1-2 M |

*Cetyltrimethylammoniumbromide, charged (1 mM = CMC)
**3-[(3-Cholamidopropyl)-dimethyl-ammonio]-1-propane sulfonate The effectiveness of the wash solution under evaluation was assessed by comparing the normalized A320 values of the neutralized elution pools. Five test solutions, Arginine, CaCl$_2$, guanidine HCl, IPA and Tris were more effective than the 1M NaCl control wash at reducing neutralized peak pool turbidity values. Arginine, CaCl$_2$, Tris and IPA were further tested using small-scale column scouting runs. A 1.1 cm (diameter)×8 cm (bed height) columns were used for these evaluations. The conditioned culture medium from CHO cell culture containing the monoclonal antibody was purified at small scale using a MabSelect™ Protein A column operated at room temperature. The load challenge was fixed at 30 mg/mL of resin for these runs. The operating conditions used for the scouting runs are summarized in Table 4. Briefly, the MabSelect™ Protein A column was equilibrated and loaded with CHO cell conditioned culture medium containing IL-13 mAb-1. The column was then washed with 5 column volumes of a high salt buffer followed by 5 column volumes of the wash solution under evaluation. The column was then washed with a series of low salt solutions in preparation for the elution step. The bound product was then eluted with 50 mM glycine, 15 mM NaCl, pH 3.0. The neutralized peak turbidity was measured by a turbidimeter, product recovery was determined by A280, and the HCP level was determined by ELISA. The results from this experiment are summarized in FIG. 3.

TABLE 4

Operating conditions used for scouting runs

| Operation | Solution Composition | Column Volumes (CVs) | Flow rate (cm hr$^{-1}$) |
|---|---|---|---|
| Equilibration | 150 mM NaCl, 20 mM Tris; pH = 7.5 | 5 | 300 |
| Load | conditioned culture medium | — | 300 |
| Post Load | 1.0 M NaCl, 20 mM Tris; pH = 7.5 | 5 | 300 |
| Flush | | | |
| Wash | Test solution | 5 | 300 |
| Pre-Elution Flush 1 | 35 mM NaCl, 50 mM Tris; pH = 7.5 | 5 | 300 |
| Pre-Elution Flush 2 | 5 mM NaCl, 10 mM Tris; pH = 7.5 | 5 | 300 |
| Elution | 15 mM NaCl, 50 mM Glycine; pH = 3.0 | 5 (3CV peak volume) | 300 |
| Strip | 6.0 M guanidine HCl | 5 | 300 |
| Storage | 16% (v/v) ethanol | 5 | 300 |
| Neutralization | 2.0 M Tris; pH 8.5 | 1% (v/v) | 300 |

Figure 3:
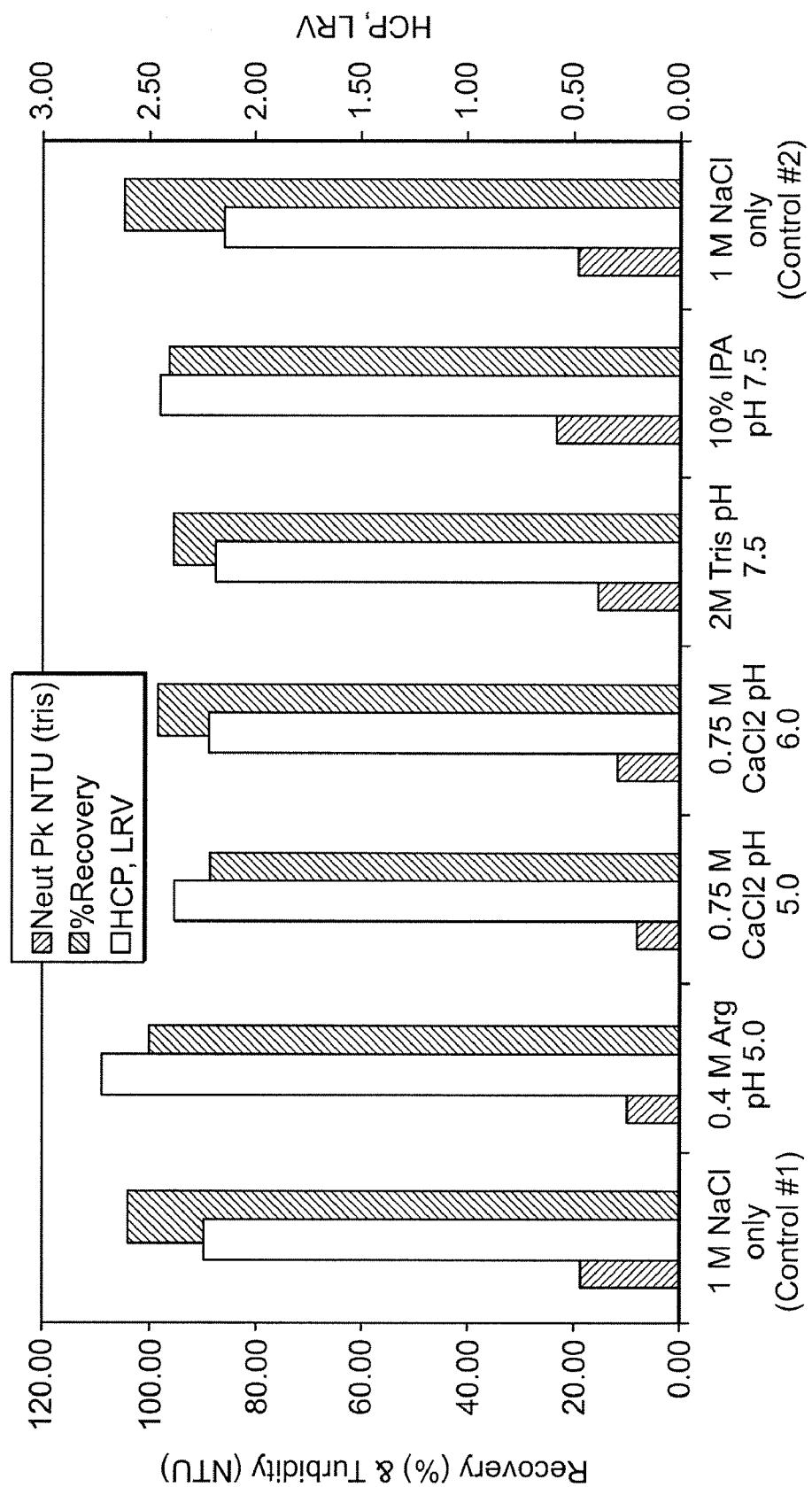
FIG. 3 is a bar graph depicting the results of experiments assaying the percent recovery (%), turbidity, HCP and LRV of IL-13 mAb-1 following a Protein A column step.

The neutralized peak pool turbidity values when the 1M NaCl control wash solution was used is ~20 NTU, and is significantly lower than that reported in Examples 1 and 2. Arginine, CaCl$_2$, and Tris were more effective at reducing neutralized peak pool turbidity compared to the 1 M NaCl control. However, of the three wash solutions that were effective for reducing neutralized peak pool turbidity, arginine was more effective for reducing HCP reduction without impacting product recovery. The HCP reduction across the MabSelect™ Protein A step with 0.4 M arginine, pH 5.0 wash was 3.5-fold higher than the corresponding values with the 1 M NaCl control wash (FIG. 3).

Example 4

IL-22 mAb

Comparison of Protein A Wash Buffers for HCP and Turbidity Reduction and Product Recovery The evaluation of several wash solutions for turbidity and HCP reduction across the Protein A column step was initially performed using a HTS method. A 25 mL column was packed with MabSelect™ resin and loaded with CHO cell conditioned media to a final load challenge of 25 mg of IL-22 mAb per mL of the resin. The resin was then slurried and 100 μL of the resin slurry was dispensed into each well of a 96-well microtiter plate. Each well of the microtiter plate was then washed with the test solution under evaluation, and the bound product was eluted with a low pH buffer. The elution pools were then neutralized with a high pH buffer and were assayed for peak turbidity by A320 and for product recovery by A280. Based on the results from the HTS experiments, test solutions that produced the highest recovery and lowest turbidity were selected for further testing using small-scale column scouting runs, the conditions for which are summarized in Table 5.

TABLE 5

Test Conditions for Column Scouting Runs

| | Test Conditions |
|---|---|
| Run 1 | Wash: 2 M Tris, pH 7.5 |
| | Elution: 50 mM glycine, 20 mM NaCl, pH 3.0 |
| | Neutralization: 2 M HEPES, pH 8.0 |
| Run 2 | Wash: 0.5 M Arginine, 50 mM Tris, pH 7.5 |
| | Elution: 50 mM glycine, 20 mM NaCl, pH 3.0 |
| | Neutralization: 2 M HEPES, pH 8.0 |

TABLE 5-continued

Test Conditions for Column Scouting Runs

| | Test Conditions |
|---|---|
| Run 3 | Wash: 2 M Tris, pH 7.5<br>Elution: 25 mM HEPES, 10 mM NaCl, pH 3.0<br>Neutralization: 2 M HEPES, pH 8.0 |
| Run 4 | Wash: 2 M Tris, pH 7.5<br>Elution: 100 mM Arginine, 10 mM NaCl, pH 3.0<br>Neutralization: 2 M HEPES, pH 8.0 |
| Run 5 | Wash: 2 M Tris, pH 7.5<br>Elution: 50 mM glycine, 20 mM NaCl, pH 3.0<br>Neutralization: 2 M Tris-base |

For each run, the 0.5 cm (d)×20 cm (h) MabSelect™ Protein A column was equilibrated with 5 column volumes (CV) of 20 mM Tris, 150 mM NaCl, pH 7.5 and subsequently loaded to approximately 35 mg product/mL resin. The column was then washed with 5 CV of the test solution. The wash phase was followed by a 3 CV pre-elution flush of 5 mM Tris, 20-30 mM NaCl, pH 7.5. The bound product was then eluted from the column with a low pH buffer and neutralized to pH 7.5 with a test solution. The column was stripped with 5 CV of 50 mM NaOH, 500 mM sodium sulfate and stored in 5 CV of 16% (v/v) ethanol, 50 mM Tris, pH 7.5. All column operations were performed at room temperature and are summarized in Table 6.

TABLE 6

Operating Conditions for Column Scouting Runs

| Operation | Solution Composition | Column Volumes (CVs) | Flow rate (cm hr$^{-1}$) |
|---|---|---|---|
| Equilibration | 150 mM NaCl, 20 mM Tris; pH 7.5 | 5 | 300 |
| Load | conditioned culture medium | — | 300 |
| Wash | Test Solution (see Table 5) | 5 | 300 |
| Pre-Elution Flush | 20-30 mM NaCl, 5 mM Tris; pH 7.5 | 3 | 300 |
| Elution | Test Solution (see Table 5) | 5 (3CV peak volume) | 300 |
| Strip | 50 mM NaOH, 500 mM sodium sulfate | 5 | 300 |
| Storage | 16% (v/v) ethanol, 50 mM Tris, pH 7.5 | 5 | 300 |
| Neutralization | Test Solution (see Table 5) | | 300 |

Figure 4:
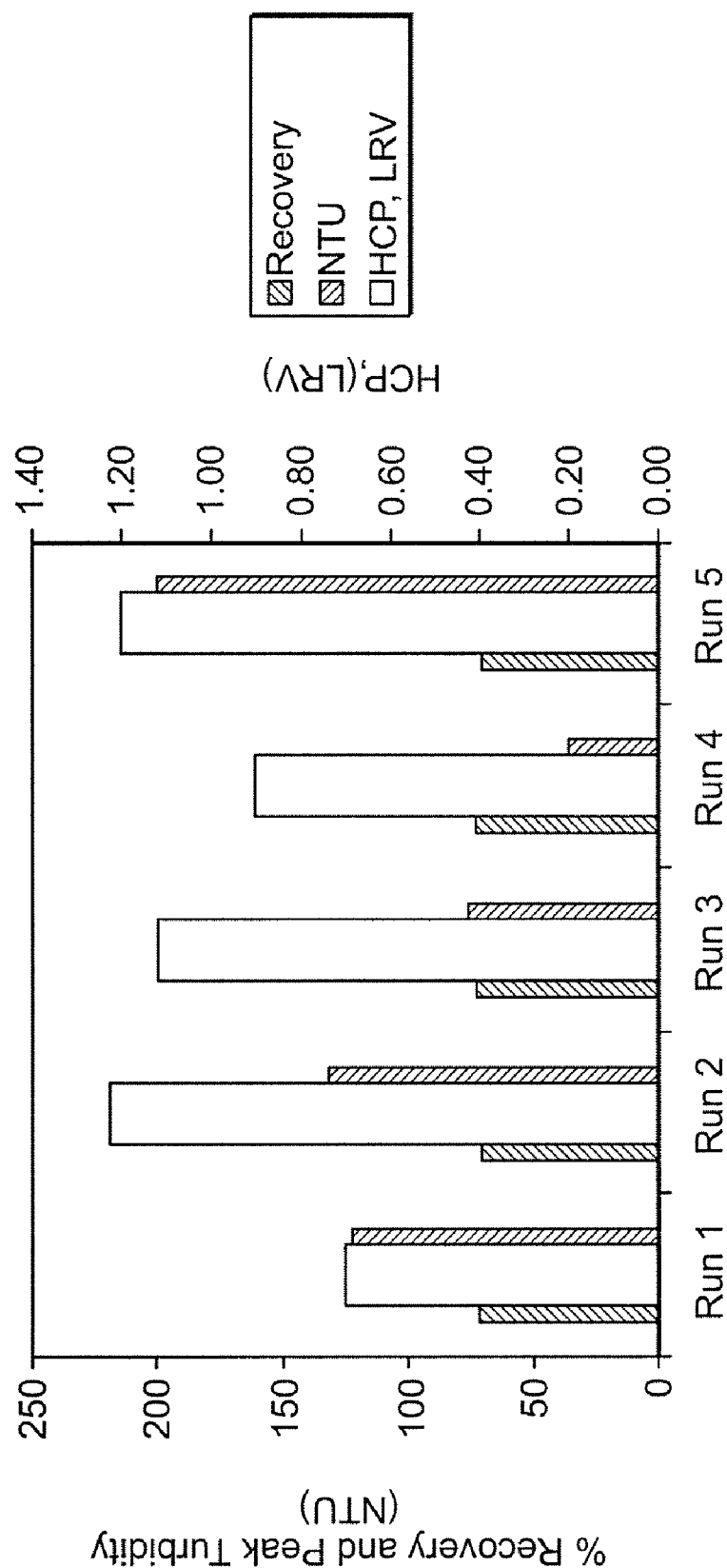
FIG. 4 is a bar graph depicting the results of experiments assaying the percent recovery (%), turbidity, HCP and LRV of IL-22 mAb following a Protein A column step.

As shown in FIG. 4, all test conditions resulted in comparable recoveries of product. The Arginine wash used in Run 2 and the Tris wash used in Run 5 provided the greatest reduction of HCP. The Arginine wash used in Run 2, however, had a nearly 2-fold lower turbidity level than the Tris Wash used in Run 5.

Example 5

RAGE mAb

Comparison of Protein A Wash Buffers for HCP and Turbidity Reduction and Product Recovery The evaluation of several wash solutions for turbidity and HCP reduction across the Protein A column step was initially performed using a HTS method. A 25 mL column was packed with MabSelect™ resin and loaded with CHO cell conditioned culture media to a final load challenge of 25 mg of RAGE mAb per mL of resin. The resin was then slurried and 100 μL of the resin slurry was dispensed into each well of a 96-well microtiter plate. Each well of the microtiter plate was then washed with the test solution under evaluation, and the bound product was eluted with a low pH buffer. The elution pools were then neutralized with a high pH buffer and were assayed for peak turbidity by A320 and for product recovery by A280. The HTS experiment resulted in acceptable recovery and turbidity for the majority of solutions tested. Based upon these results and prior experience, arginine was evaluated and chosen as the wash condition for this product.

The 5 cm (d)×23 cm (h) MabSelect™ Protein A column was equilibrated with 5 column volumes (CV) of 20 mM Tris, 150 mM NaCl, pH 7.5 and subsequently loaded to approximately 35 mg product/mL resin. The column was then washed with 5 CV of 0.5 M Arginine, 50 mM Tris, pH 7.5. The wash phase was followed by a 3 CV pre-elution flush of 39 mM NaCl, 5 mM Tris, pH 7.5. The bound product was then eluted from the column with 22 mM NaCl, 50 mM Glycine, pH 3.0 and neutralized to pH 7.5 with 2.0 M Tris, pH 8.2. The column was stripped with 5 CV of 50 mM NaOH, 500 mM sodium sulfate and stored in 5 CV of 16% (v/v) ethanol, 50 mM Tris, pH 7.5. All column operations were performed at room temperature and are summarized in Table 7.

TABLE 7

Operating Conditions for Column Scouting Runs

| Operation | Solution Composition | Column Volumes (CVs) | Flow rate (cm hr$^{-1}$) |
|---|---|---|---|
| Equilibration | 150 mM NaCl, 20 mM Tris; pH 7.5 | 5 | 300 |
| Load | conditioned culture medium | — | 300 |
| Wash | 0.5 M Arginine, 50 mM Tris, pH 7.5 | 5 | 300 |
| Pre-Elution Flush | 39 mM NaCl, 5 mM Tris; pH 7.5 | 3 | 300 |
| Elution | 22 mM NaCl, 50 mM Glycine; pH 3.0 | 5 (3CV peak volume) | 300 |
| Strip | 50 mM NaOH, 500 mM sodium sulfate | 5 | 300 |
| Storage | 16% (v/v) ethanol, 50 mM Tris, pH 7.5 | 5 | 300 |
| Neutralization | 2.0 M Tris, pH 8.2 | 0.9% (v/v) | 300 |

Figure 5:
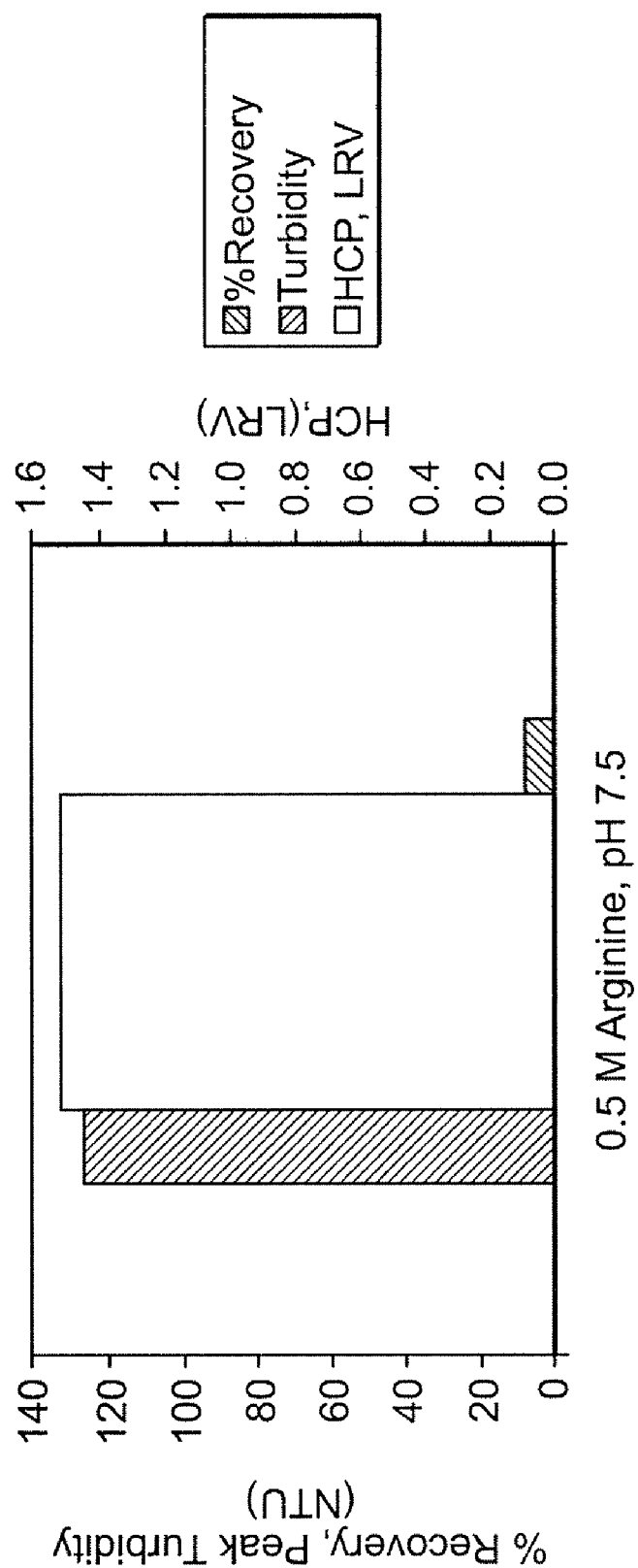
FIG. 5 is a bar graph depicting the results of experiments assaying the percent recovery (%), turbidity, HCP and LRV of RAGE mAb following a Protein A column step.

As shown in FIG. 5, the arginine wash resulted in acceptable recovery of product, while providing desirable levels of HCP removal and reduction in neutralized peak turbidity.

Example 6

A-Beta mAb

Comparison of Protein A Wash Buffers for HCP and Turbidity Reduction and Product Recovery The evaluation of various wash solutions was first performed using a high throughput screening (HTS) method. A MabSelect Protein A column was initially loaded with conditioned media from a Chinese Hamster Ovary (CHO) cell culture process. The MabSelect resin was then slurried and 100 uL of the resin slurry was dispensed into each well of a 96-well microtiter plate. Each well of the microtiter plate was then washed with a test solution under evaluation (see Table 8), and subsequently eluted with a low pH buffer. The elution pool from each well was assayed for peak turbidity by A320 and for product recovery by A280. Based on the results from the HTS experiments, the test solutions that produced the highest recovery and highest HCP removal were selected for further testing using small-scale column runs. These wash solutions were Arginine and $CaCl_2$.

TABLE 8

HTS Wash Solutions Tested

| Wash Excipient | Concentration |
| --- | --- |
| NaCl | 0.5M, 1.0M, 1.5M, 2.0M |
| Arginine | 0.5M, 1.0M, 1.5M, 2.0M |
| $CaCl_2$ | 0.5M, 1.0M, 1.5M, 2.0M |
| Tris | 0.5M, 1.0M, 1.5M, 2.0M |

In the column runs, a 1.6 cm (diameter)×15 cm (bedheight) column was used for these evaluations. The MabSelect Protein A column was equilibrated with a buffer containing 50 mM Tris, 0.15M NaCl pH 7.5, and loaded with CHO cell conditioned media containing A-Beta mAb to 40 mg/mL. The column was then flushed with 2 column volumes (CV) of the equilibration buffer, and subsequently washed with 5 CV's of either Arginine or $CaCl_2$. The column was then washed with 10 mM Tris, 10 mM NaCl pH 7.5 in preparation for the elution step. The bound product was subsequently eluted with 50 mM glycine, 10 mM NaCl pH 3.0. The neutralized peak turbidity was measured by A320 or by a turbidimeter, product recovery was determined by A280, and the HCP level was determined by an ELISA. Table 9 summarizes the column operating conditions for all experiments described in this Example.

TABLE 9

Protein A Column Operating Conditions

| Column Operation | Solution Composition | Volume (CVs) | Linear Velocity (cm/hr) |
| --- | --- | --- | --- |
| Equilibration | 50 mM Tris, 0.15M NaCl pH 7.5 | 5 | <300 |
| Load | conditioned culture medium | NA | <300 |
| Post Load Flush | 50 mM Tris, 0.15M NaCl pH 7.5 | 2 | <300 |
| Wash 1: | 50 mM Tris pH 7.5  0.5M Arginine | 5 | <300 |
| | w/  1.0M Arginine | | |
| | 0.5M $CaCl_2$ | | |
| | 1.0M $CaCl_2$ | | |
| Wash 2 | 10 mM Tris, 10 mM NaCl pH 7.5 | 5 | <300 |
| Elution | 50 mM glycine, 10 mM NaCl pH 3.0 | 4 | <300 |
| Neutralization | 2M Hepes pH 8.5 or 2M Tris pH 9.0 | ~1% | <300 |
| Strip | 50 mM NaOH, 0.5M sodium sulfate | 5 | <300 |
| Strip Wash | 50 mM Tris, 0.15M NaCl pH 7.5 | 5 | <300 |
| Storage | 16% (v/v) ethanol | | <300 |

TABLE 10

Protein A Data for Wash Studies

| Wash Conditions | % Recovery by A280 | HCP ppm |
| --- | --- | --- |
| 0.5 M Arginine | 87 | 9300 |
| 0.5 M Arginine | 87 | 12,700 |
| 0.5 M CaCl2 | 86 | 9000 |
| 0.5 M CaCl2 | 80 | 10,600 |
| 1.0 M CaCl2 | 80 | 11,500 |

Table 10 shows the results for recovery and HCP values for the wash experiments for A-Beta mAb. Arginine and CaCl2 were comparable wash solutions for reduction of host cell protein and final peak pool turbidity. 0.5M Arginine was chosen as the wash solution for the A-Beta mAb process based the lower loss of product during the wash.

Example 7

IL-13 mAb-2

Comparison of Protein A Wash Buffers for HCP and Turbidity Reduction and Product Recovery The evaluation of several wash solutions for turbidity reduction across the Protein A column step was initially performed using a high throughput screening (HTS) method. A 25 mL column was packed with MabSelect™ resin and loaded with CHO conditioned media to a final load challenge of 50 mg of IL-13 mAb-2 per mL of resin. The resin was then slurried and 100 uL of the resin slurry was dispensed into each well of a 96-well microtiter plate. Each well of the microtiter plate was then washed with a test solution under evaluation, the bound product was eluted, and the acidic elution pool neutralized.

For the HTS, various excipient washes, elution buffers and titrants, were utilized combinatorially and with varying concentrations. Excipient washes utilized in the HTS were calcium chloride, sodium chloride, Tris, and arginine. Elution buffers utilized in the HTS were glycine, HEPES, and acetic acid together with varying concentrations of NaCl. Titrants utilized in the HTS were Tris, HEPES and Imidazole.

Using A320 as a surrogate for precipitation, the effectiveness of the wash solutions was assessed by comparing the normalized A320 values of the neutralized elution pools. Arginine proved most effective at reducing the A320 readings of the eluted peak. Based on the results from the HTS experiments, test solutions that produced the highest recovery and lowest turbidity were selected for further testing using small-scale column scouting runs. This lead to the further testing of calcium chloride, arginine, and sodium chloride (control) as wash buffers in small-scale column trials.

The conditioned culture medium from a CHO culture process containing IL-13 mAb-2 was purified at small scale using a MabSelect™ Protein A column operated at room temperature. Column sizes used for the initial evaluation were 1.1 cm in diameter with bed heights from 20 cm to 25 cm. The load challenge was fixed at 35 mg/mL of resin for these runs. The conditions used for the scouting runs are summarized in Table 11.

TABLE 11

Operating conditions used for scouting runs

| Operation | Solution Composition | Column Volumes (CVs) | Flow rate (cm hr − 1) |
|---|---|---|---|
| Equilibration | 150 mM NaCl, 50 mM Tris; pH = 7.5 | 5 | 300 |
| Load | conditioned culture medium | — | 240 |
| Post Load Flush | 150 mM NaCl, 50 mM Tris; pH = 7.5 | 5 | 300 |
| Wash | Test solution (see Table 12) | 5 | 300 |
| Pre-Elution Flush | 10 mM Tris, NaCl concentration equal to elution buffer, pH = 7.5 | 3 | 300 |
| Elution | See Table 13 | 6 CV (3 CV peak volume) | 300 |
| Strip | 50 mM NaOH, 500 mM sodium sulfate | 5 | 180 |
| Storage | 16% (v/v) ethanol, 50 mM Tris, 150 mM NaCl, pH = 7.5 | 5 | 300 |
| Neutralization | See Table 13 | ~1-5% (v/v) | |

TABLE 12

List of wash solutions evaluated

| Reference | Solution Composition |
|---|---|
| 1 | 0.5 M arginine, 20 mM Tris, pH 7.5 |
| 2 | 0.5 M calcium chloride, 20 mM Tris, pH 7.5 |
| 3 | 0.5 M sodium chloride, 20 mM Tris, pH 7.5 |
| 4 | 2.0 M arginine, 20 mM Tris, pH 7.5 |
| 5 | 1.5 M calcium chloride, 20 mM Tris, pH 7.5 |
| 6 | 1.0 M arginine, 20 mM Tris, pH 7.5 |
| 7 | 1.0 M calcium chloride, 20 mM Tris, pH 7.5 |
| 7 | 2.0 M arginine, 20 mM Tris, pH 7.5 |

TABLE 13

List of elution and titration buffers employed

| Reference | Elution Buffer |
|---|---|
| A | 50 mM glycine, 20 mM NaCl, pH 3.1 |
| B | 50 mM glycine, 50 mM NaCl, pH 3.1 |
| C | 50 mM acetic acid, 20 mM NaCl, pH 3.1 |
| | Titrant |
| D | 2.0 M Tris, pH 9.0 |
| E | 2.0 M HEPES, pH 9.0 |
| F | 1.0 M Imidazole, pH 8.0 |

Figure 6:
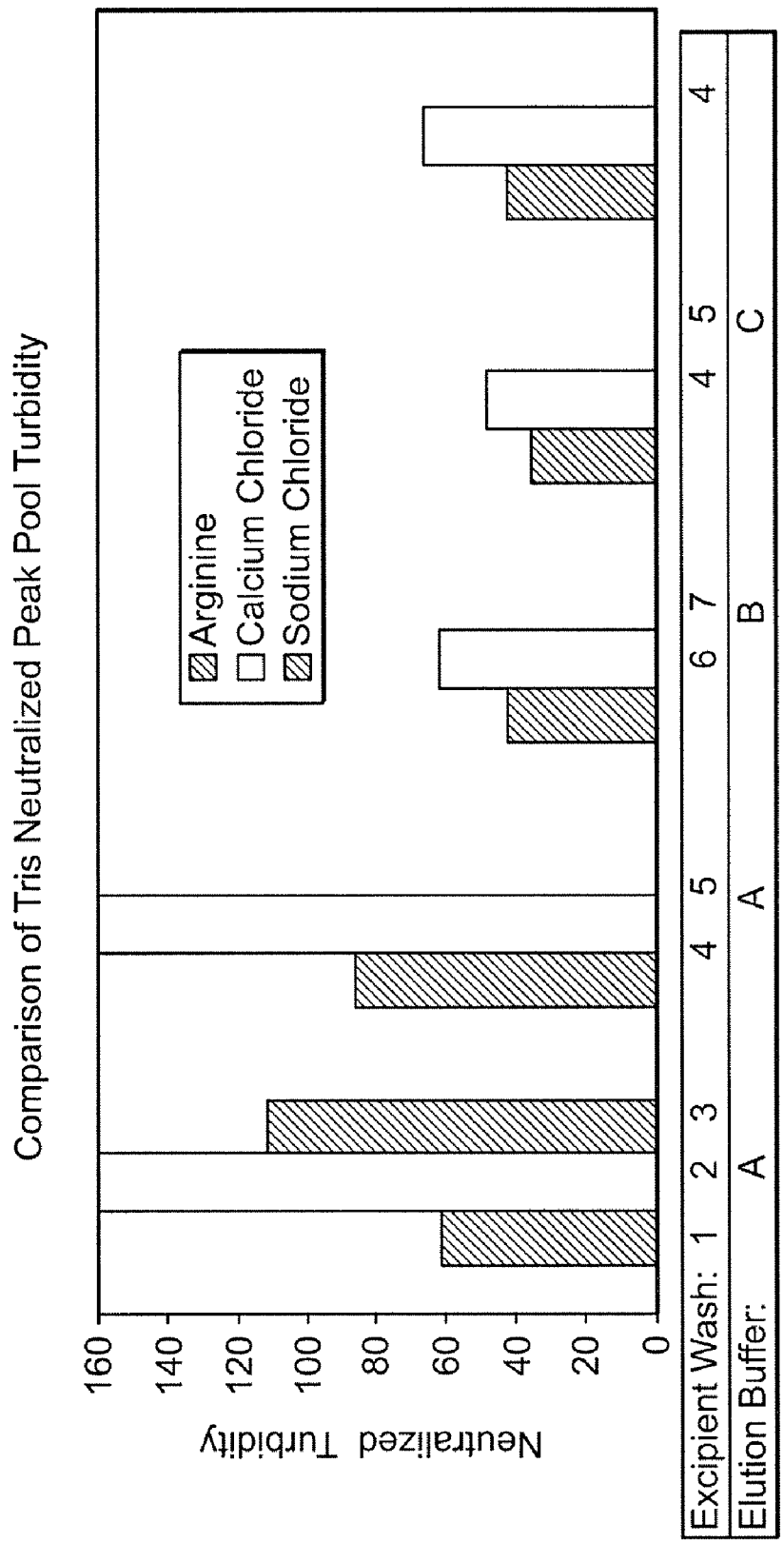
FIG. 6 is a bar graph depicting the results of experiments assaying the turbidity IL-13 mAb-2 following a Protein A column step.

Briefly, the MabSelect™ Protein A column was equilibrated and loaded with CHO conditioned medium containing IL-13 mAb-2. The column was then washed with 5 CVs of a moderate salt buffer followed by 5 CVs of the wash solution under evaluation. The column was then washed with 3 CVs of a low salt solution in preparation for the elution step. The bound product was then eluted with solution containing either glycine or acetic acid as the buffering species with a pH of 3.1. This peak pool was then independently neutralized with three different titrants. The neutralized peak turbidity was measured with a turbidimeter, product recovery was measured by A280, and the HCP level was quantified with ELISA. The results from this experiment are summarized in FIG. 6.

At every concentration trialed and with various elution buffers (see Table 13), arginine was found to be more effective than calcium chloride or sodium chloride at reducing acidic and neutralized peak pool turbidity. This finding was consistent whether the acidic pools were neutralized with Tris, HEPES, or imidazole titrant (see Table 13).

In addition, it was demonstrated that the effect of an arginine wash was not restricted to a final, discrete pH of the neutralized pool. Across a pH range of 7.5-8.2 (e.g., 7.5, 7.7, 7.9, 8.0, 8.1, and 8.2), the neutralized peak turbidity values decrease as the pH increases. Across this same range, however, the employment of arginine wash always resulted in a lower NTU than if calcium chloride was used.

The recovery of loaded product was >95% for each excipient wash trialed. HTS data indicated that measurably less recovery would be obtained by washing with >1.5 M calcium chloride, which is why this concentration was not trialed.

The examined wash species could not be differentiated based on the final concentration of HCP, HMW, and Protein A in the peak pool. However, an analysis of the wash fraction eluted with a 1.0 M arginine wash consistently revealed significant levels of HCP. HCP levels in the wash fraction were ~49000 ppm while only ~22000 ppm in the peak. This is evidence that the arginine wash selectively removes HCP.

All references cited herein are incorporated herein by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A method for isolating a product, the method comprising:
   (a) providing a load fluid comprising a product and one or more impurities, wherein the product is an Fc-containing monoclonal antibody;
   (b) contacting the load fluid with a medium, wherein the medium is a Protein A chromatography column, and wherein the medium can bind the product under conditions suitable for binding the product, thereby providing a bound medium;
   (c) contacting the bound medium with one or more wash solutions, wherein at least one wash solution comprises an arginine derivative, thereby providing a washed medium, wherein the arginine derivative is acetyl arginine, agmatine, arginic acid, N-alpha-butyroyl-L-arginine or N-alpha-pyvaloyl arginine;
(d) contacting the washed medium with an elution solution under conditions suitable for eluting the product, and
(e) collecting an eluate comprising the product.

2. The method of claim 1, wherein the monoclonal antibody is specific for GDF-8.

3. The method of claim 1, wherein the monoclonal antibody is specific for IL-13.

4. The method of claim 1, wherein the monoclonal antibody is specific for IL-22.

5. The method of claim 1, wherein the monoclonal antibody is specific for RAGE.

6. The method of claim 1, wherein the monoclonal antibody is specific for A-Beta.

7. The method of claim 1, wherein the concentration of arginine derivative in the wash solution is about 0.1 M to about 2.0 M.

8. The method of claim 1, wherein the concentration of arginine derivative in the wash solution is about 0.1 M to about 0.9 M.

9. The method of claim 1, wherein the concentration of arginine derivative in the wash solution is about 1.1 M to about 2.0 M.

10. The method of claim 1, wherein the concentration of arginine derivative in the wash solution is about 0.5 M.

11. The method of claim 1, wherein the pH of the wash solution is about 4.5 to about 8.0.

12. The method of claim 1, wherein the pH of the wash solution is greater than 4.5 and less than about 8.0.

13. The method of claim 1, wherein the pH of the wash solution is about 7.5.

14. The method of claim 1, wherein one or more of the impurities are a host cell protein, a nucleic acid, a product variant, or an endotoxin.

15. The method of claim 1, wherein one or more of the impurities is a virus or fragment thereof.

16. The method of claim 1, wherein the elution solution comprises at least one of sodium chloride, arginine or an arginine derivative, glycine, HEPES, and acetic acid, wherein the arginine derivative is acetyl arginine, agmatine, arginic acid, N-alpha-butyroyl-L-arginine, or N-alpha-pyvaloyl argmine.

17. The method of claim 1, wherein the elution solution has a pH of between about 2 and about 4.

18. The method of claim 1, wherein the eluate comprises an isolated product and the purity of the isolated product is increased compared to a corresponding method in which less than about 0.1 M of arginine derivative is used in a wash solution.

19. The method of claim 1, wherein the eluate comprises an isolated product, and wherein the ratio of the product to at least one impurity is increased compared to a corresponding method in which no detectable amount of arginine derivative is used in a wash solution.

20. The method of claim 1, wherein the eluate comprises an isolated product, and wherein the ratio of the product to host cell protein is increased compared to a corresponding method in which less than about 0.1 M of arginine derivative is used in a wash solution.

21. The method of claim 1, wherein the eluate comprises a product, and wherein the ratio of the product to host cell protein is increased compared to a corresponding method in which no detectable amount of arginine derivative is used in a wash solution.

22. The method of claim 1, wherein the turbidity of the eluate is reduced compared to a corresponding method in which less than about 0.1 M of arginine derivative is used in a wash solution.

23. The method of claim 1, wherein the turbidity of the eluate is reduced compared to a corresponding method in which no detectable amount of arginine derivative is used in a wash solution.

24. The method of claim 1, wherein in step (a), at least one impurity is bound to the product and in step (c), contacting the bound medium with one or more wash solutions removes said at least one impurity that is bound to the product.

25. The method of claim 1, wherein the concentration of arginine derivative in the wash solution is about 1.0 M.

26. A method for isolating an antibody, the method comprising:
(a) providing a load fluid comprising the antibody and one or more impurities, wherein the antibody is an Fc-containing monoclonal antibody;
(b) contacting the load fluid with a Protein A medium, wherein the medium can bind the antibody under conditions suitable for binding the antibody, thereby providing a bound medium;
(c) contacting the bound medium with one or more wash solutions, wherein at least one wash solution comprises an arginine derivative in a concentration of about 0.1 M to about 2.0 M, thereby providing a washed medium, wherein the arginine derivative is acetyl arginine, agmatine, arginic acid, N-alpha-butyroyl-L-arginine or N-alpha-pyvaloyl arginine;
(d) contacting the washed medium with an elution solution under conditions suitable for eluting the antibody; and
(e) collecting an eluate comprising the antibody,
wherein the ratio of the antibody to host cell protein in the eluate is increased and wherein the eluate has reduced turbidity compared to an eluate recovered in a corresponding method in which no detectable amount of arginine derivative is used in a wash solution.

27. The method of claim 26, wherein in step (c) the pH of the wash solution is about 4.5 to about 8.0.

28. The method of claim 26, wherein the concentration of arginine derivative in the wash solution is about 0.1 M to about 0.9 M.

29. The method of claim 28, wherein the pH of the wash solution is about 4.5 to about 8.0.

30. The method of claim 28, wherein the method does not comprise anionic upstream adsorptive filtration.

31. The method of claim 26, wherein the concentration of arginine derivative in the wash solution is about 1.1 M to about 2.0 M.

32. The method of claim 26, wherein the concentration of arginine derivative in the wash solution is about 0.5 M.

33. The method of claim 6, wherein the concentration of arginine derivative in the wash solution is about 1.0 M.

34. A method for reducing turbidity in an eluate comprising a product, the method comprising:
(a) providing a load fluid comprising the product and one or more impurities, wherein the product is an Fc-containing monoclonal antibody;
(b) contacting the load fluid with a medium, wherein the medium is a Protein A chromatography column, and wherein the medium can bind the product under conditions suitable for binding the product, thereby providing a bound medium;
(c) contacting the bound medium with one or more wash solutions, wherein at least one wash solution comprises an arginine derivative, thereby providing a washed medium, wherein the arginine derivative is acetyl arginine, agmatine, arginic acid, N-alpha-butyroyl-L-arginine or N-alpha-pyvaloyl arginine;

(d) contacting the washed medium with an elution solution under conditions suitable for eluting the product, thereby generating an eluate comprising the product; and (e) adjusting the pH of the eluate to between about 6.5 and about 8.2, wherein the eluate has reduced turbidity compared to a corresponding method in which less than about 0.1M of arginine derivative is used in a wash solution.

35. The method of claim 34, wherein in step (c) the wash solution comprises an arginine derivative in a concentration of about 0.1 M to about 2.0 M.

36. The method of claim 34, wherein in step (c) the wash solution comprises an arginine derivative in a concentration of about 0.1 M to about 0.9 M.

37. The method of claim 34, wherein in step (c) the wash solution comprises an arginine derivative in a concentration of about 1.1 M to about 2.0 M.

38. The method of claim 34, wherein in step (c) the wash solution comprises an arginine derivative in a concentration of about 0.5 M.

39. The method of claim 34, wherein the pH of the wash solution is about 4.5 to about 8.0.

40. The method of claim 34, wherein the method does not comprise anionic upstream adsorptive filtration.

41. The method of claim 34, wherein the concentration of arginine derivative in the wash solution is about 1.0 M.

42. A method for reducing turbidity and impurities in an eluate comprising a product, the method comprising:

(a) providing a load fluid comprising the product and one or more impurities, wherein the product is an Fc-containing monoclonal antibody;

(b) contacting the load fluid with a medium, wherein the medium is a Protein A chromatography column, and wherein the medium can bind the product under conditions suitable for binding the product, thereby providing a bound medium;

(c) contacting the bound medium with one or more wash solutions, wherein at least one wash solution comprises an arginine derivative, thereby providing a washed medium, wherein the arginine derivative is acetyl arginine, agmatine, arginic acid, N-alpha-butyroyl-L-arginine or N-alpha-pyvaloyl arginine;

(d) contacting the washed medium with an elution solution under conditions suitable for eluting the product, thereby generating an eluate comprising the product; and (e) adjusting the pH of the eluate to between about 6.5 and about 8.2, wherein the ratio of the product to at least one impurity in the eluate is increased and the eluate has reduced turbidity compared to a corresponding method in which less than about 0.1M arginine derivative is used in a wash solution.

43. The method of claim 42, wherein in step (c) the concentration of the arginine derivative in the wash solution is about 0.1 M to about 2.0 M.

44. The method of claim 42, wherein in step (c) the concentration of the arginine derivative in the wash solution is about 0.1 M to about 0.9 M.

45. The method of claim 42, wherein in step (c) the concentration of the arginine derivative in the wash solution is about 1.1 M to about 2.0 M.

46. The method of claim 42, wherein in step (c) the concentration of the arginine derivative in the wash solution is about 0.5 M.

47. The method of claim 42, wherein the concentration of arginine derivative in the wash solution is about 1.0 M.

* * * * *